US009993812B2

(12) United States Patent
Komati et al.

(10) Patent No.: US 9,993,812 B2
(45) Date of Patent: Jun. 12, 2018

(54) HIGH ACTIVITY CATALYST FOR HYDROSILYLATION REACTIONS AND METHODS OF MAKING THE SAME

(71) Applicant: MOMENTIVE PERFORMANCE MATERIALS INC., Waterford, NY (US)

(72) Inventors: Srinivas Komati, Suryapet (IN); Vivek Khare, Bangalore (IN); Kenrick Lewis, Flushing, NY (US); Alok Sarkar, Malda (IN); Abirami Srikanth, Bangalore (IN); Aroop Kumar Roy, Mechanicville, NY (US)

(73) Assignee: MOMENTIVE PEREFORMANCE MATERIALS INC., Waterford, NY (US)

( * ) Notice: Subject to any disclaimer, the term of this patent is extended or adjusted under 35 U.S.C. 154(b) by 0 days. days.

(21) Appl. No.: 14/373,223

(22) PCT Filed: Mar. 14, 2013

(86) PCT No.: PCT/US2013/031377
§ 371 (c)(1),
(2) Date: Jul. 18, 2014

(87) PCT Pub. No.: WO2013/158272
PCT Pub. Date: Oct. 24, 2013

(65) Prior Publication Data
US 2015/0051357 A1 Feb. 19, 2015

Related U.S. Application Data

(60) Provisional application No. 61/625,320, filed on Apr. 17, 2012.

(51) Int. Cl.
*B01J 31/06* (2006.01)
*B01J 37/02* (2006.01)
(Continued)

(52) U.S. Cl.
CPC ............. *B01J 31/069* (2013.01); *B01J 23/42* (2013.01); *B01J 23/96* (2013.01); *B01J 31/06* (2013.01);
(Continued)

(58) Field of Classification Search
None
See application file for complete search history.

(56) References Cited

U.S. PATENT DOCUMENTS 3,875,293 A    4/1975   Stouthamer et al.
4,127,594 A    11/1978   Anderson et al.
(Continued)

FOREIGN PATENT DOCUMENTS

CN           1930197 A    3/2007
CN        101426574 A    5/2009
(Continued)

OTHER PUBLICATIONS

Chauhan et al., "Synthesis, stabilization, and applications of nanoscopic siloxane-metal particle conjugates," Journal of Organometallic Chemistry, 686, 2003, pp. 24-31.*
(Continued)

*Primary Examiner* — Marc S Zimmer
(74) *Attorney, Agent, or Firm* — Joseph Waters; McDonald Hopkinds LLC

(57) ABSTRACT

A heterogeneous catalyst comprising a metal-containing polymer matrix covalently bonded to a support material and a method of making and using such catalysts. The metal-containing polymer matrix comprises metal nano-particles encapsulated in a polymer matrix, e.g., a siloxane. In one aspect, the metal-containing polymer matrix can be bonded to the support material via a hydrophobic group attached to the support material. The catalyst can be recovered after being used in a metal catalyzed reaction and exhibit excellent catalytic activity upon reuse in subsequent reactions.

47 Claims, 4 Drawing Sheets

(51) Int. Cl.

| | | |
|---|---|---|
| *B01J 37/16* | (2006.01) | |
| *B01J 23/42* | (2006.01) | |
| *B01J 23/96* | (2006.01) | |
| *B01J 35/00* | (2006.01) | |
| *B01J 35/02* | (2006.01) | |
| *C07C 5/08* | (2006.01) | |
| *C07F 7/08* | (2006.01) | |
| *C08G 65/336* | (2006.01) | |
| *B01J 31/12* | (2006.01) | |
| *B01J 31/40* | (2006.01) | |

(52) U.S. Cl.
CPC .......... *B01J 31/126* (2013.01); *B01J 31/127* (2013.01); *B01J 35/002* (2013.01); *B01J 35/0013* (2013.01); *B01J 35/023* (2013.01); *B01J 37/0209* (2013.01); *B01J 37/0211* (2013.01); *B01J 37/0236* (2013.01); *B01J 37/16* (2013.01); *C07C 5/08* (2013.01); *C07F 7/0836* (2013.01); *C07F 7/0879* (2013.01); *C08G 65/336* (2013.01); *B01J 31/4038* (2013.01); *B01J 2231/40* (2013.01); *B01J 2231/4211* (2013.01); *B01J 2231/4261* (2013.01); *B01J 2231/645* (2013.01); *B01J 2231/70* (2013.01); *B01J 2231/76* (2013.01); *Y02P 20/582* (2015.11)

(56) References Cited

U.S. PATENT DOCUMENTS

| | | | |
|---|---|---|---|
| 4,236,024 A | 11/1980 | Matsuda et al. | |
| 4,424,162 A | 1/1984 | Rosen | |
| 4,552,986 A | 11/1985 | Isogai et al. | |
| 5,134,109 A | 7/1992 | Uchiyama et al. | |
| 5,214,227 A | 5/1993 | Zhou et al. | |
| 5,380,906 A | 1/1995 | Nishihira et al. | |
| 6,001,241 A | 12/1999 | Gosling et al. | |
| 6,087,523 A | 7/2000 | Bank et al. | |
| 6,096,936 A | 8/2000 | Fukunaga et al. | |
| 6,177,585 B1* | 1/2001 | Chen | C07F 7/0829 556/479 |
| 6,420,615 B1 | 7/2002 | Chaudhari et al. | |
| 6,551,960 B1 | 4/2003 | Laine et al. | |
| 6,608,129 B1 | 8/2003 | Koloski et al. | |
| 6,815,570 B1 | 11/2004 | Negiz et al. | |
| 7,053,021 B1* | 5/2006 | Zhong | B22F 1/0018 502/185 |
| 7,521,392 B1 | 4/2009 | Kilic et al. | |
| 2002/0068807 A1 | 6/2002 | Breunig et al. | |
| 2002/0077514 A1 | 6/2002 | Rossi et al. | |
| 2003/0045425 A1 | 3/2003 | Ruth et al. | |
| 2003/0194600 A1 | 10/2003 | Pan | |
| 2004/0087441 A1* | 5/2004 | Bock | B01J 23/462 502/313 |
| 2005/0101819 A1 | 5/2005 | Galperin et al. | |
| 2005/0233896 A1 | 10/2005 | Carter et al. | |
| 2006/0128565 A1 | 6/2006 | Flytzani-Stephanopoulos et al. | |
| 2006/0281938 A1 | 12/2006 | Weissman et al. | |
| 2007/0031722 A1 | 2/2007 | Adzic et al. | |
| 2007/0093669 A1* | 4/2007 | Le-Khac | C07D 301/06 549/536 |
| 2007/0135299 A1 | 6/2007 | Lee et al. | |
| 2007/0254804 A1 | 11/2007 | Doni et al. | |
| 2008/0020923 A1 | 1/2008 | Debe et al. | |
| 2008/0058200 A1 | 3/2008 | Kobayashi et al. | |
| 2008/0085820 A1 | 4/2008 | Majkrzak | |
| 2008/0117949 A1 | 5/2008 | Sukhman et al. | |
| 2008/0206555 A1 | 8/2008 | Choi et al. | |
| 2008/0206562 A1* | 8/2008 | Stucky | B01J 23/74 428/403 |
| 2008/0220296 A1 | 9/2008 | Eichhorn et al. | |
| 2009/0018301 A1 | 1/2009 | Thomas et al. | |
| 2009/0143607 A1 | 6/2009 | Kobayashi et al. | |
| 2009/0215615 A1 | 8/2009 | Mao et al. | |
| 2009/0227743 A1 | 9/2009 | Hashimoto et al. | |
| 2009/0286899 A1 | 11/2009 | Hofmann et al. | |
| 2015/0051357 A1* | 2/2015 | Komati | B01J 37/0236 525/523 |

FOREIGN PATENT DOCUMENTS

| | | | |
|---|---|---|---|
| DE | 19840255 A | 3/2000 | |
| EP | 190695 A | 6/1992 | |
| EP | 1213053 A | 6/2002 | |
| EP | 1739104 A | 1/2007 | |
| EP | 1987880 A | 11/2008 | |
| GB | 709616 A | 5/1954 | |
| GB | 914282 A | 1/1963 | |
| GB | 1123837 A | 8/1968 | |
| GB | 1174779 A | 12/1969 | |
| GB | 1287054 A | 8/1972 | |
| GB | 1347475 A | 2/1974 | |
| GB | 2310384 A | 8/1997 | |
| JP | 2002-134123 A | * | 5/2002 |
| JP | 2009-208027 A | 9/2009 | |
| WO | 2004000458 A | 12/2003 | |
| WO | 2006038045 A | 4/2006 | |
| WO | 2009122149 A1 | 10/2009 | |
| WO | 2009139747 A | 11/2009 | |
| WO | 2009139748 A | 11/2009 | |
| WO | 2014094169 A | 6/2014 | |

OTHER PUBLICATIONS

Chauhan et al., "Synthesis, stabilization, and applications of nanoscopic siloxane-metal particle conjugates", Journal of Organometallic Chemistry, vol. 686, 2003, pp. 24-31.*

"Engineered Polymer for Controlled Metal Nanoparticle Synthesis" authored by Fu et al. and published in the journal entitled Chemistry of Materials (2010) 22, 2181-2183.*

"Chiral Bisphosphine BINAP-Stabilized Gold and Palladium Nanoparticles with Small Size and their Palladium Nanoparticle-Catalyzed Asymmetric Reaction" authored by Tamura et al. and published in the Journal of the American Chemical Society (2003), 125(51), 15742-15743.*

"C—O Hydrogenolysis Catalyzed by PD-PMHS Nanoparticles in the Company of Chloroarenes" authored by Rahaim et al. and published in Organic Letters (2011) 13(4), 584-587.*

"Polysiloxane-Pd Nanocomposites as Recyclable Chemoselective Hydrogenation Catalysts" authored by Chauhan et al. and published in JACS (2004) 8493-8500.*

"Sol Gel Synthesis of Nanosilver Embedded Hybrid Materials using COmbined Organosilica Precursors" authored by Zhai et al. and published in Journal of Sol-Gel Science & Technology (2012) 62, 281-286.*

International Search Report and Written Opinion of the International Searching Authority, PCT/US2013/031377, dated May 23, 2013.

Luo, Zhixin, CN Notification of the First Office Action for Application No. 201380020160.6, State Intellectual Property Office of People's Republic of China, report dated Sep. 17, 2015, China.

Luo, Zhixin, CN Notification of the Second Office Action for Application No. 201380020160.6, State Intellectual Property Office of People's Republic of China, report dated Jun. 3, 2016, CN.

Goebel, Matthias, Partial Supplementary European Search Report for Application No. 13778484.9 PCT/US2013031377, dated Dec. 14, 2015, European Patent Office, Germany.

Goebel, Matthias, Extended European Search Report for Application No. 13778484.9 PCT/US2013031377, dated May 1, 2016, European Patent Office, Germany.

Toshima, Naoki et al., "Substrate selectivity by the polymer support in hydrogenation over crosslinked polymer-immobilized metal catalysts", Reactive Polymers, vol. 15, Nov. 1, 1991, pp. 135-145, Elsevier Science Publishers, Amsterdam, NL.

Meltzer, Sheffer et al., "Fabrication of nanostructures by hydroxylamine seeding of gold nonoparticle templates", Langmuir, American Chemical Society, vol. 17, No. 5, 2001, pp. 1713-1718.

(56) References Cited

OTHER PUBLICATIONS

Nang, Hongshui et al., "Mechanisms of PVP in the preparation of silver nanoparticles", Materials Chemistry and Physics, Elsevier B.V., vol. 94, 2005, pp. 449-453.

Shim, Jaehee et al., "Carbon-supported platinum nanoparticles synthesized by plasma-chemical reduction method for fuel cell applications", Journal of the Electrochemical Society, vol. 154 (2), 2007, pp. B165-B169.

Shimizu, Takami et al., "Size evolution of alkanethiol-protected gold nanoparticles by heat treatment in the solid state", J Phys Chem B, vol. 107, 2003, pp. 2719-2724.

Vracar, Lj. M. et al., "Electrocatalysis by nanoparticles—oxygen reduction on Ebonex/Pt electrode", Journal of Electroanalytical Chemistry, vol. 587, 2006, pp. 99-107.

Duff, Daniel G. et al., "Formation of a polymer-protected platinum sol: a new understanding of the parameters controlling morphology", J Phys Chem, vol. 99, 1995, pp. 15934-15944.

Zeng, Jianhuang. et al., " Activities of Pt/C catalysts prepared by low temperature chamical reduction methods", Applied Catalysis A: General 308, 2006, pp. 99-104.

Wu, Chunwei et al., "Rapid synthesis of gold and platinum nanoparticles using metal displacement reduction with sonomechanical assistance", Chemistry of Materials , vol. 18, Jun. 27, 2006, pp. 2925-2928.

Du YK, Yang P. et al., "Thermal decomposition behaviors of PVP coated on platinum nanoparticles", Journal of Applied Polymer Science, vol. 99, Jan. 5, 2006, pp. 23-26.

\* cited by examiner

HIGH ACTIVITY CATALYST FOR HYDROSILYLATION REACTIONS AND METHODS OF MAKING THE SAME

CROSS REFERENCE TO RELATED APPLICATIONS

This application is a 35 U.S.C. 371 national stage filing and claims priority to PCT Application No. PCT/US2013/031377, entitled "High Activity Catalyst for Hydrosilylation Reactions and Methods of Making the Same," filed Mar. 14, 2013, which claims the benefit of U.S. Provisional Patent Application No. 61/625,320 entitled "High Activity Catalyst for Hydrosilylation Reactions and Methods of Making the Same," filed on Apr. 17, 2012, both of which are incorporated by reference herein in their entirety.

FIELD

The present invention provides heterogeneous catalyst materials suitable for use in catalyzing a variety of reactions including, for example, hydrosilylation reactions. In particular, the present invention provides metal catalyst compositions containing metal nanoparticles such as, for example, platinum nanoparticles. More specifically, the present invention provides metal nanoparticles encapsulated in a polymer matrix, which metal-containing matrix is bonded to a support material.

BACKGROUND

Heterogeneous catalysts have advantages over homogenous catalysts including the ability to recycle and reuse the catalyst, and the absence of the active catalyst species in the reaction products. Usually, a heterogeneous catalyst consists of catalytically active particles deposited on support particles that are catalytically inactive (e.g., silica, alumina, etc.). In a few cases, the support particles are themselves catalytically active. The catalytically active particles are deposited onto the support by techniques such as impregnation of the catalytic particles, adsorption of catalyst species from a solution, homogeneous deposition precipitation onto a support, and chemical vapor deposition. The catalytic activity of the heterogeneous catalysts generally depends upon factors such as specific surface area, pore structure of the support particles, and the size of the active particles on the support. While these factors may be adjusted to try and increase catalytic activity, the catalytic activity of heterogeneous catalysts is usually lower than that of homogeneous catalysts, on a weight basis.

One attempt to increase catalyst activity has involved reducing the size of the active particles to nanoscale dimensions. Due to this, supported nano Pt catalysts in particular have gained tremendous attraction. The nano size of the Pt metal increases intrinsic catalytic activity through an increase in the surface to volume ratio and the specific surface area. (See U.S. Pat. No. 7,053,021.) Many of the existing methods for synthesizing supported nanoparticulate Pt catalysts, however, are the same as those used for synthesizing normal supported catalysts, i.e., impregnation, adsorption, homogeneous deposition, and chemical vapor deposition. In all of these, only physical interactions (Van der Waals forces, e.g.) exist between the catalytically active particles and the support. The physical interactions may not be strong enough to withstand the shear conditions in stirred or fixed bed reactors, especially for catalytically active particles of nano-size. Such catalysts are vulnerable to loss of the catalytically active particles to the reaction medium. This could significantly limit their recycle/reuse potential.

U.S. Patent Publication No. 2004/0087441A1 describes PtRu nanoparticles directly applied to the support by reducing precursor metal salts and depositing the nanoparticles on the support during synthesis. It may be noted that in such a catalyst the attractive forces between the active nanoparticles and the support are physical forces, and this may not provide sufficiently strong binding between the two. Such catalysts are likely to be vulnerable to nanoparticle loss in the high shear conditions of fixed bed and stirred reactors.

Other attempts to improve catalytic activity have involved adjusting the crystal structure, softness, etc., of the nanoparticles. For example, U.S. Pat. No. 6,177,585 describes the use of bi-metallic catalysts, although the catalyst particles are not in the nano size range.

One issue in prior catalyst systems is stabilization of the particles because the nanoparticles tend to aggregate in the absence of stabilizing agents. Traditionally, nanoparticle stabilization is achieved by using surfactants. Stabilization provided by surfactants is considered to be of an electrostatic nature. Steric stabilization of particles may be accomplished by encapsulating the nanoparticles in a crosslinked siloxane polymer as described in B.P.S. Chauhan et. al, Journal of Organometallic Chemistry, 686(1-2), p. 24-31, 2003. Such nanoparticles are reported to be catalytically active, capable of being separated from the product liquid by ultracentrifugation, and reused. However, ultracentrifugation is not a cost-effective method of separating the nanoparticles for industrial scale processes.

SUMMARY

The present invention provides a nanoparticle heterogeneous metal catalyst and methods for making such catalysts. In one embodiment, the catalysts possess high catalytic activity. In one embodiment, the catalysts are reusable and exhibit excellent stability and activity upon reuse. The catalysts can also be recovered via simple filtration techniques and do not require the use of expensive separation columns.

In one aspect, the present invention stabilizes metal particles sterically through encapsulation in a cross linked siloxane polymeric matrix, and simultaneously anchors the cross linked siloxane polymer to silica particles via covalent bonding linkages. These particles can be easily separated by filtration, which is a more cost-effective means of recovering the catalyst for industrial scale processes.

In one aspect, the present invention provides heterogeneous catalyst comprising a metal-containing polymer matrix covalently bonded to a support material.

In one embodiment, the metal-containing polymer matrix comprises metal nanoparticles encapsulated in a polymer matrix chosen from an organic polymer matrix or a siloxane polymer matrix.

In one embodiment, the polymer matrix comprises an organic polymer matrix comprising a polymer or copolymer of a vinyl aromatic, a vinyl halide, an alpha monoolefin, an acrylonitrile, an acrylate, an amide, an acrylamide, an ester, or a combination of two or more thereof.

In one embodiment, the polymer matrix is derived from a silicon hydride-containing polyorganohydrosiloxane of the general formula:

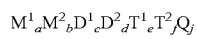

wherein: $M^1 = R^1R^2R^3SiO_{1/2}$; $M^2 = R^4R^5R^6SiO_{1/2}$; $D^1 = R^7R^8SiO_{2/2}$; $D^2 = R^9R^{10}SiO_{2/2}$; $T^1 = R^{11}SiO_{3/2}$;

$T^2 = R^{12}SiO_{3/2}$; $Q = SiO_{4/2}$; $R^1$, $R^2$, $R^3$, $R^4$, $R^5$, $R^6$, $R^7$, $R^8$, $R^9$, $R^{10}$, $R^{11}$, and $R^{12}$ are aliphatic, aromatic or fluoro monovalent hydrocarbon having from 1 to 60 carbon atoms; at least one of $R^4$, $R^9$, $R^{12}$ is hydrogen; and the subscript a, b, c, d, e, f, and j are zero or positive subject to the following limitations: $2 \leq a+b+c+d+e+f+j \leq 6000$, and $b+d+f>0$.

In one embodiment, the polymer matrix comprises a functional group chosen from a hydride; a carboxyl group, an alkoxy functional group, an epoxy functional group, a triaz-1-yn-2-ium functional group, an anhydride group, a mercapto group, an acrylate, an alkyl, an olefinic, a dienyl, or a combination of two or more thereof.

In one embodiment, the polymer matrix comprises a functional group chosen from $-S_i-H$; $-Si(CH_2)_n COOR^{13}$, $-Si(CH_2)nSi(OR^{14})_3$, $-Si(OR^{15})_{1-3}$, $-S_i-(CH_2)_n$-epoxy, $-Si-(CH_2)_n-N\equiv N$, etc. where $R^{13}$, $R^{14}$, and $R^{15}$ is chosen from hydrogen, hydrocarbyl, substituted hydrocarbyl, or a combination of two or more thereof, and n is chosen from 1 to 26.

In one embodiment, the polymer matrix comprises a polysiloxane. In one embodiment, the polysiloxane is formed from a hydrosiloxane and a vinyl silicon compound.

In one embodiment, the metal nanoparticles are chosen from nanoparticles of aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, oxides and sulfides of such metal, or combinations of two or more thereof.

In one embodiment, the metal-containing polymer matrix has a ratio of polymer to metal of from about 1:1000 to about 100:1; from about 1:1 to about 20:1; from about 10:1 to about 20:1; even from about 12:1 to about 16:1.

In one embodiment, the metal particles have a particle size of from about 1 to about 100 nanometers.

In one embodiment, the support material is chosen from silicon, a silicate such as a sodium silicate, a borosilicate, or a calcium aluminum silicates, clay, silicate, silica, starch, carbon, alumina, titania, calcium carbonate, barium carbonate, zirconia, metal oxide, carbon nanotubes, synthetic and natural zeolites, polymeric resins in bead or fibrous form, or and mixtures of two or more thereof.

In one embodiment, the metal loading ranges from about 0.001 to 20 percent by weight of the support material; from about 0.05 to about 5 percent by weight of the support material; even from about 0.1 to about 1 percent by weight of the support material.

In one embodiment, the support material comprises a functional group chosen from a group such as silanol, alkoxy, acetoxy, silazane, oximino-functional silyl group, hydroxyl, acyloxy, ketoximino, amine, aminoxy, alkylamide, hydrogen, allyl, an aliphatic olefinic group, aryl, hydrosulfide, or a combination of two or more thereof.

In one embodiment, the support material comprises a functional group chosen from $-Si-CH=CH_2$, $-Si-OH$, $-Si-(CH_2)_nC\equiv CH$, $-Si-(CH_2)_n-NH_2$, $-Si-(CH_2)_n-OH$, $-Si-(CH_2)_n-SH$, or a combination of two or more thereof, and n is 1-26, 1-10, even 1-8.

In one embodiment, the metal-containing polymer matrix is covalently bonded to the support material via a hydrophobic functional group attached to the support material. In one embodiment, the hydrophobic group is chosen from an alkyldisilazane, a vinyl-containing silazane, or a combination thereof.

In one aspect, the present invention provides a metal catalyzed reaction employing a catalyst in accordance with the present invention including aspects and embodiments of such catalysts described above and in the detailed description. In one embodiment, the reaction is chosen from a hydrosilylation reaction, a hydroxylation reaction, a silaesterification reaction, a hydrogenation reaction, a oxidation reaction, a Heck and Suzuki coupling reaction, a dehydrocoupling reaction.

In another aspect, the present invention provides a method of synthesizing supported nanosized metal catalysts, the method comprising (a) forming a metal-containing polymer matrix comprising metal nanoparticles encapsulated in a polymer matrix; and (b) attaching the metal-containing polymer matrix to a support material via covalent chemical bonds.

The method of claim 22 wherein forming the metal-containing polymer matrix comprises forming a colloidal suspension of metal nano-particles by reacting metal complexes with a silicon hydride-containing polyorganohydrosiloxane solution in suitable solvent under nitrogen atmosphere, and encapsulating the metal nano-particles in a siloxane matrix.

In one embodiment, the metal complex is selected from a metal salt chosen from $PtCl_2$, $H_2PtCl_6$, $Pt_2(dba)_3$, $Pt_2(dvs)_3$, $Pt(OAc)_2Pt(acac)_2$, $Na_2PtCl_6$, $K_2PtCl_6$, platinum carbonate, platinum nitrate, 1,5-cycooctadienedimethylplatinum(II), platinum perchlorate, amine complexes of the platinum ammonium hexachloropalladate(IV), palladium(II) chloride, $AuCl_3$, $Au_2O_3$, $NaAuO_2$, $AgCl$, $AgNO_3$, $CuSO_4$, $CuO$, $Cu(NO_3)_2$, $CuCl_2$, $Ru_2O_3$, $RuCl_2$, $FeCl_2 \cdot 6H_2O$, $ZnCl_2$, $CoCl_2 \cdot 6H_2O$, $NiCl_2 \cdot 6H_2O$, $MnCl_2 \cdot 4H_2O$, $TiCl_4$, vanadium chloride, cadmium chloride, calcium chloride, zirconium tetrachloride, mercuric chloride complexes, or a combination of two or more thereof.

In one embodiment, the silicon hydride-containing polyorganohydrosiloxane is of the general formula:

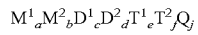

wherein: $M^1 = R^1R^2R^3SiO_{1/2}$; $M^2 = R^4R^5R^6SiO_{1/2}$; $D^1 = R^7R^8SiO_{2/2}$; $D^2 = R^9R^{10}SiO_{2/2}$; $T^1 = R^{11}SiO_{3/2}$; $T^2 = R^{12}SiO_{3/2}$; $Q = SiO_{4/2}$; $R^1$, $R^2$, $R^3$, $R^4$, $R^5$, $R^6$, $R^7$, $R^8$, $R^9$, $R^{10}$, $R^{11}$, and $R^{12}$ are aliphatic, aromatic or fluoro monovalent hydrocarbon having from 1 to 60 carbon atoms; at least one of $R^4$, $R^9$, $R^{12}$ is hydrogen; and the subscript a, b, c, d, e, f, and j are zero or positive subject to the following limitations: $2 \leq a+b+c+d+e+f+j \leq 6000$, and $b+d+f>0$.

In one embodiment, encapsulating the metal nano-particles in the siloxane matrix comprises exposing the colloidal suspension to the presence of oxygen for a time period of from about 10 to about 30 minutes.

In one embodiment, the method comprises an optional step of removing at least about 50% of the solvent from the colloidal solution.

In one embodiment, the ratio of polymer to metal complex ranges from about 0.001 to about 100.

In one embodiment, the molecular weight of the polysiloxanes range from 100 to 50000, and the Si—H content of the polysiloxanes ranges from 0.001 to 99 mole percent.

In one embodiment, the nanoparticles are chosen from at least one of aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, oxides and sulfides thereof.

In one embodiment, the polymer matrix comprises a functional group chosen from a hydride; a carboxyl group, an alkoxy functional group, an epoxy functional group, a triaz-1-yn-2-ium functional group, an anhydride group, a mercapto group, an acrylate, an alkyl, or a combination of two or more thereof.

In one embodiment, the polymer matrix comprises a functional group chosen from —S$_i$—H; —Si(CH$_2$)$_n$COOR$^{13}$, —Si(CH$_2$)nSi(OR$^{14}$)$_3$, —Si(OR$^{15}$)$_{1-3}$, —S$_i$(CH$_2$)$_n$-epoxy, —Si—(CH$_2$)$_n$—N—N≡N, etc. where R$^{13}$, R$^{14}$, and R$^{15}$ is chosen from hydrogen, hydrocarbyl, substituted hydrocarbyl, or a combination of two or more thereof, and n is chosen from 1 to 26.

In one embodiment, the support material is chosen from silicon, a silicate such as sodium silicate, a borosilicate, or a calcium aluminum silicate, clay, silica, starch, carbon, alumina, titania, calcium carbonate, barium carbonate, zirconia, metal oxide, carbon nanotubes, synthetic and natural zeolites, polymeric resins in bead or fibrous form, or a mixture of two or more thereof.

In one embodiment, the reaction is carried out at a temperature between about 5 degree C. to about 150 degree C., and at a pressure ranging from 0.001 bar to 10 bar.

In one embodiment, the nanoparticles have a size in the range of from about 1 to about 100 nanometers.

In one embodiment, the reaction is carried out in the presence or absence of suitable solvents.

In one embodiment, the method further comprises drying the supported nanoparticle catalysts In one embodiment, the support material comprises particles having a size in the range from 50 to 1000 micrometers.

In one embodiment, the ratio of metal loading to support material ranges from about 0.001 to 20 percent by weight.

In one embodiment, the support material comprises a functional group chosen from a group such as silanol, alkoxy, acetoxy, silazane, oximino-functional silyl group, hydroxyl, acyloxy, ketoximino, amine, aminoxy, alkylamide, hydrogen, allyl, an aliphatic olefinic group, aryl, hydrosulfide, or a combination of two or more thereof.

In one embodiment, the support material comprises a functional group chosen from —Si—CH═CH$_2$, —Si—OH, —Si—(CH$_2$)$_n$C≡CH, —Si—(CH$_2$)$_n$—NH$_2$, —Si—(CH$_2$)$_n$—OH, —Si—(CH$_2$)$_n$—SH, or a combination of two or more thereof, and n is 1-26, 1-10, even 1-8.

In one embodiment, the support material is functionalized with a hydrophobic group.

In one embodiment, the hydrophobic group is chosen from an alkyldisilazane, a vinyl-containing silazane, trimethyl disilazane, tetramethyl disilazane, pentamethyl disilazane, hexamethyl disilazane, octamethyl trisilazane, hexamethylcyclo trisilazane, tetraethyltetramethylcyclo tetrasilazane, tetraphenyldimethyl disilazane, dipropyltetramethyl disilazane, dibutyltetramethyl disilazance, dihexyltetramethyl disilazane, dioctyltetramethyl disilazane, diphenyltetramethyl disilazane, octamethylcyclo tetrasilazane, vinyltriacetoxysilane and vinyltrialkoxysilanes, or a combination of two or more thereof.

In still another aspect, the present invention provides a process comprising: (a) conducting a metal catalyzed reaction with a catalyst comprising a metal-containing polymer matrix covalently bonded to a support material; (b) recovering the catalyst; and (c) conducting a subsequent metal catalyzed reaction with the recovered catalyst.

In one embodiment, the metal catalyzed reaction is chosen from hydrosilylation, hydroxylation, silaesterification, hydrogenation, oxidation, Heck and Suzuki coupling, dehydrocoupling. In one embodiment, the metal catalyzed reaction comprise a hydrosilylation reaction comprising reacting a silicon hydride with an unsaturated reactant.

In one embodiment, the silicon hydride is selected from a group described by (a) the formula

wherein: M$^1$=R$^1$R$^2$R$^3$SiO$_{1/2}$; M$^2$=R$^4$R$^5$R$^6$SiO$_{1/2}$; D$^1$=R$^7$R$^8$SiO$_{2/2}$; D$^2$=R$^9$R$^{10}$SiO$_{2/2}$; T$^1$=R$^{11}$SiO$_{3/2}$; T$^2$=R$^{12}$SiO$_{3/2}$; Q=SiO$_{4/2}$; R$^1$, R$^2$, R$^3$, R$^4$, R$^5$, R$^6$, R$^7$, R$^8$, R$^9$, R$^{10}$, R$^{11}$, and R$^{12}$ are aliphatic, aromatic or fluoro monovalent hydrocarbon having from 1 to 60 carbon atoms; at least one of R$^4$, R$^9$, R$^{12}$ is hydrogen; and the subscript a, b, c, d, e, f, and j are zero or positive subject to the following limitations: 2≤a+b+c+d+e+f+j≤6000, and b+d+f>0, or (b) a monomer having a general formula R'$_m$H$_n$SiX$_{4-m-n}$, where each R' is independently selected from the group consisting of alkyls comprising one to 20 carbon atoms, cycloalkyls comprising four to 12 carbon atoms, and aryls; m=0 to 3, n=1 to 3, and m+n=1 to 4; each X is independently selected from a OR' group or a halide. In one embodiment, the silicon hydride is chosen from trimethylsilane, dimethylsilane, triethylsilane, dichlorosilane, trichlorosilane, methyldichlorosilane, dimethylchlorosilane, ethyldichlorosilane, cyclopentlydichlorosilane, methylphenylchlorosilane, (3,3,3-trifluoropropyl), heptamethyltrisiloxane hydride, triethoxysilane, trimethoxysilane, hydrogen terminated polydimethylsiloxane, monochlorosilane, or a combination of two or more thereof.

In one embodiment, the unsaturated reactant is selected from the group consisting of a hydrocarbon compound or an unsaturated polyether.

In one embodiment, the hydrocarbon compound is described by one or more of the formulas (CH$_2$═CH(CH$_2$)$_g$)$_n$R'$_i$Si(OR')$_{4-h-i}$ and (CH$_2$═CH(CH$_2$)$_g$R'$_i$SiCl$_{4-h-i}$, where R' is independently selected from the group consisting of alkyls comprising one to 20 carbon atoms, cycloalkyls comprising four to 12 carbon atoms, and aryls; g is 0 to 20, h is 1 to 3, I is 0-3, and h+i is 1 to 4.

In one embodiment, the hydrocarbon compounds is chosen from 1-hexene and 1-5 hexadiene, trans-2hexene, styrene, allylmethoxytriglycol, alpha-methylstyrene, eugenol, 1-octene, allyl glycidylether, trivinylcyclohexane, allylmethacrylate, allylamine, trichloroethylene, allyl and vinyl ethers, dichlorostyrene, or a combination of two or more thereof.

In one embodiment, the unsaturated polyether is chosen from a blocked or random polyoxyalkylenes having at least one of the general formulas:

 (X);

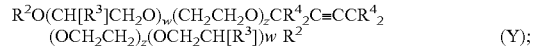 (Y);

or

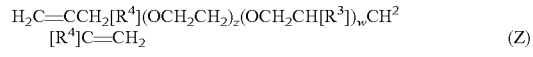 (Z)

where R$^1$ denotes an unsaturated organic group containing from 3 to 10 carbon atoms; R$^2$ is hydrogen, or a polyether capping group of from 1 to 8 carbon atoms chosen from an alkyl group, an acyl group, or a trialkylsilyl group; R$^3$ and R$^4$ are monovalent hydrocarbon groups chosen from a C$_1$-C$_{20}$ alkyl group, an aryl group, an alkaryl group, or a cycloalkyl group; R$^4$ can also be hydrogen; z is 0 to 100 inclusive and w is 0 to 100 inclusive, with the proviso that z+w>0.

In one embodiment, the process comprises repeating steps (b) and (c) two or more times. In one embodiment, the process comprises repeating steps (b) and (c) five times.

In one embodiment, the recovered catalyst has a catalytic activity substantially similar to activity of the catalyst in step (a). In one embodiment, the recovered catalyst has a catalytic activity that is at least 85% of the catalytic activity of the catalyst in step (a). In one embodiment, the recovered catalyst has a catalytic activity that is at least 95% of the catalytic activity of the catalyst in step (a). In one embodiment, the recovered catalyst has a catalytic activity that is at least 99% of the catalytic activity of the catalyst in step (a).

In one embodiment, the reaction is carried out in a batch, semi batch, or continuous mode at a temperature between about 0 degree C. to 500 degree C. and a pressure ranging from 0.01 bar to 100 bar.

In one embodiment, recovering the catalyst is accomplished by filtration.

These and other aspects and embodiments of the invention are further understood with reference to the drawings and detailed description.

BRIEF DESCRIPTION OF THE DRAWINGS

FIG. 2a shows a magnification of 135,000; FIG. 2b shows a magnification of 650,000.

DETAILED DESCRIPTION

Figure 1:
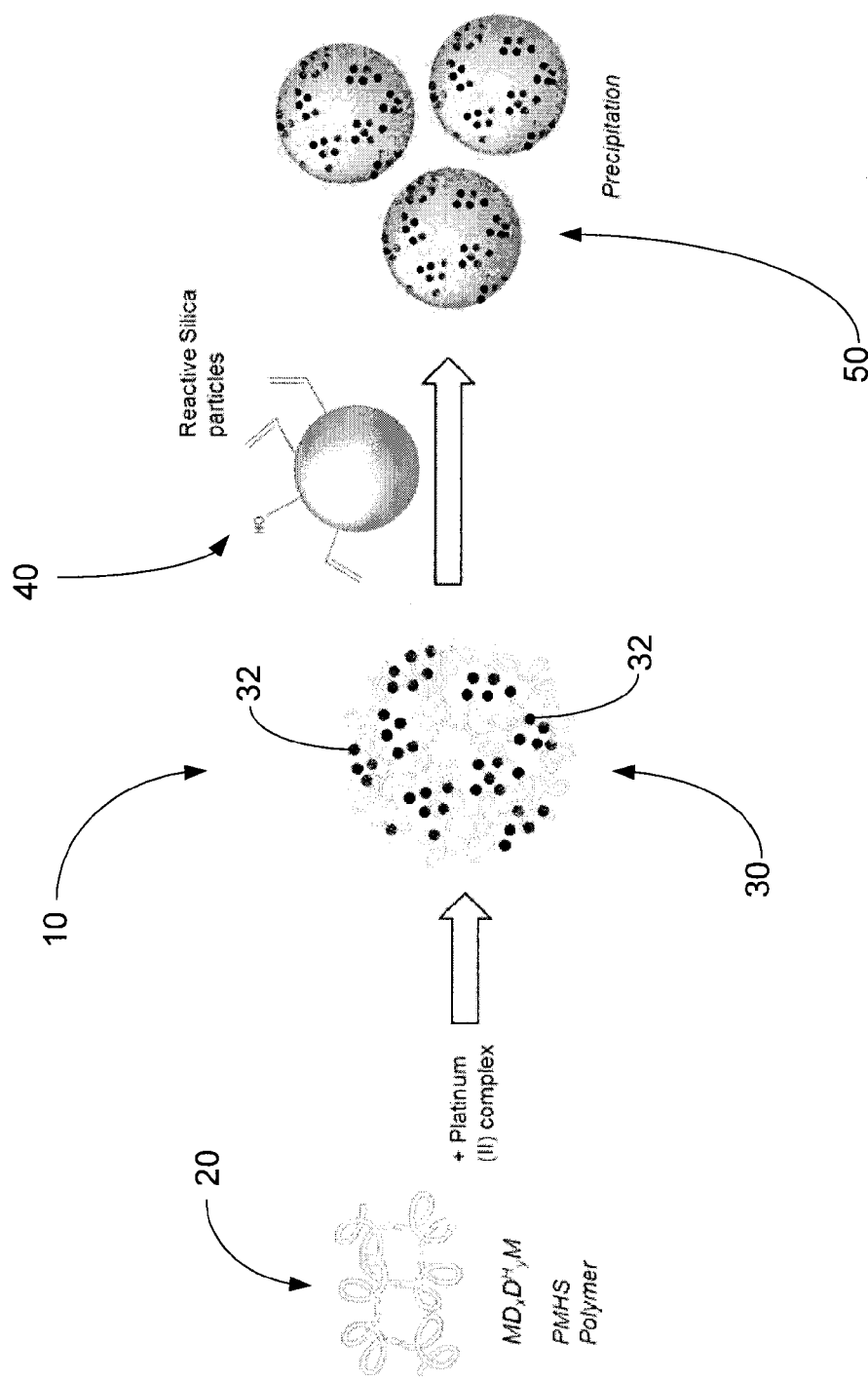
FIG. 1 is a schematic illustration of metal catalysts in accordance with aspects of the invention and a scheme for forming the same.

The present invention provides a heterogeneous metal catalyst comprising metal nanoparticles. In one embodiment, a heterogeneous metal catalyst material comprises a metal-containing polymer matrix bonded to a support material. The metal-containing polymer matrix comprises a polymer matrix having a plurality of metal nanoparticles disposed in the polymer matrix. The support material comprises a substrate having functional groups at or near the substrates surface that are capable of bonding with the metal-containing polymer matrix material.

Metal-containing Polymer Matrix

The metal-containing polymer matrix comprises a polymer matrix comprising a plurality of metal nanoparticles dispersed in the polymer matrix. In one embodiment, the metal nanoparticles are encapsulated in the polymer matrix. The polymer matrix may be selected as desired for a particular purpose or intended use. For example, the polymer matrix may be chosen to provide a particular functionality for bonding with the substrate material or based on the environment in which the catalyst will be used.

In one embodiment, the polymer matrix can comprise an organic synthetic polymer material. Suitable organic synthetic polymer materials include, but are not limited to thermoplastic polymers, thermoplastic elastomers, etc. Suitable organic polymer materials can include polymers or copolymers of vinyl aromatic monomers, such as styrene; vinyl halide such as vinyl chloride; acrylonitrile; alpha-monoolefins such as ethylene, propylene, etc.; acrylates; acrylamides; amides; esters; etc., or a combination of two or more thereof.

In one embodiment, the polymer matrix comprises a cross linked polysiloxane network. The polysiloxane network can comprise a crosslinked or partially crosslinked network of hydrosiloxanes or hydride fluid with a vinyl silicon compound. In one embodiment, the hydrosiloxanes are polyorganohydrosiloxanes comprising a silicon hydride (Si—H) group. In one embodiment, the polyorganohydrosiloxane is of Formula (1):

$$M^1{}_aM^2{}_bD^1{}_cD^2{}_dT^1{}_eT^2{}_fQ_j. \qquad (1)$$

wherein: $M^1=R^1R^2R^3SiO_{1/2}$; $M^2=R^4R^5R^6SiO_{1/2}$; $D^1=R^7R^8SiO_{2/2}$; $D^2=R^9R^{10}SiO_{2/2}$; $T^1=R^{11}SiO_{3/2}$; $T^2=R^{12}SiO_{3/2}$; $Q=SiO_{4/2}$; $R^1, R^2, R^3, R^4, R^5, R^6, R^7, R^8, R^9, R^{10}, R^{11}$, and $R^{12}$ are independently aliphatic, aromatic, cycloaliphatic, or fluoro monovalent hydrocarbon having from 1 to 60 carbon atoms, and at least one of $R^4, R^9$, and $R^{12}$ is hydrogen. Examples of useful aliphatic groups include, but are not limited to, methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl, isooctyl groups, and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Examples of suitable aryl groups include, but are not limited to, phenyl, naphthyl; o-, m- and p-tolyl, xylyl, ethylphenyl, and benzyl. $R^4, R^9, R^{12}$ are independently selected from hydrogen. The subscripts a, b, c, d, e, f, and j are zero or positive subject to the following limitations: $2 \le a+b+c+d+e+f+j \le 6000$, $b+d+f>0$. The Si—H content of the polysiloxanes can range from 0.001 to 99 mole percent.

The polysiloxane can comprise a variety of functionalities to allow the metal-containing polymer matrix to be bonded or adhered to the support material. Examples of suitable functional groups include, but are not limited to, hydride functionalities (—$S_iH$); carboxyl functional groups, alkoxy functional groups, epoxy functional groups, a triaz-1-yn-2-ium functional group, an anhydride group, a mercapto group, an acrylate, an alkyl, olefinic, dienyl, etc. or a combination of two or more thereof. Non-limiting examples of suitable functional groups include —$S_i$—H; —Si$(CH_2)_n$COOR$^{13}$, —Si$(CH_2)$nSi$(OR^{14})_{1-3}$, —$S_i(CH_2)_n$-epoxy, —Si—$(CH_2)_n$—N—N≡N, etc. where $R^{13}, R^{14}$, and $R^{15}$ can be hydrogen, hydrocarbyl, substituted hydrocarbyl, or a combination of two or more thereof, and n can be 1 to 26, 2 to 10, even 2 to 8.

In one embodiment, the polymer matrix comprises a polyalkyl hydrosiloxane, a polyaryl hydrosiloxane, or a combination of two or more thereof. In one embodiment, the polymer matrix comprises a hydrosiloxane chosen from poly(methyl hydrosiloxane) (PMHS), poly(ethyl hydrosiloxane), poly(propyl hydrosiloxane), polyaryl hydrosiloxane (e.g., poly(phenyl hydrosiloxane), poly(tolyl hydrosiloxane)), poly(phenyl dimethylhydrosiloxy)siloxane, poly(dimethyl siloxane co-methyl hydrosiloxane), poly(methyl hydrosiloxane co-phenyl methyl siloxane), poly(methyl hydrosiloxane coalkyl methyl siloxane), poly(methyl hydrosiloxane co-diphenyl siloxane), poly(methyl hydrosiloxane co-phenyl methyl siloxane). The hydrosiloxane can be a homopolymer or a copolymer comprising two or more hydrosiloxanes.

The vinyl silicon compound is not particularly limited and can be, for example, a cyclic vinyl siloxane, a non-cyclic vinyl siloxane etc. Examples of suitable vinyl siloxanes includes, but are not limited to, 1,3-divinyl-1,1,3,3-tetramethyl disoloxane, 1,3,5 trimethyl-1,3,5-trivinyl-cyclotrisiloxane, 1,3,5,7-tetramethyl-1,3,5,7-tetravinyl-cyclotetrasiloxane, etc.

The molecular weight of the polysiloxanes of the present invention can range from 150 to 50000, 200 to 30000, 250 to 25000, 300 to 15000, even 500 to 10000. Here as elsewhere in the specification and claims, numerical values can be combined to form new and non-disclosed ranges. It will be appreciated that the polysiloxane network may have some residual hydride bonds.

The metal nanoparticle material is not particularly limited and can be chosen as desired for a particular purpose or intended use. The metal-containing polymer matrix comprises nanoparticles chosen from nanoparticles of aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, oxides and sulfides of such metals, or a combination of two or more nanoparticles thereof. In one embodiment, the nanoparticles comprise alloys of two or more metals. In one embodiment, the metal nanoparticles comprise platinum.

In one embodiment, the metal nanoparticles have a particle size of from about 1 to about 100 nanometers (nm). In another embodiment, the metal nanoparticles have a particle size of from about 5 to about 90 nanometers. In still another embodiment, the metal nanoparticles have a particle size of from about 10 to about 80 nanometers. In yet another embodiment, the metal nanoparticles have a particle size of from about 20 to about 70 nanometers (nm). In an even further embodiment, the metal nanoparticles have a particle size of from about 30 to about 60 nanometers (nm). In yet a further embodiment, the metal nanoparticles have a particle size of from about 35 to about 50 nanometers (nm). Here as elsewhere in the specification and claims, numerical values may be combined to form new or undisclosed ranges. The particle size of the metal nanoparticles may be determined by any suitable method. In one embodiment, particle size is determined by transmission electron microscopy (TEM).

In one embodiment, the weight ratio of polymer to metal is from about 1:1000 to about 100:1. In another embodiment, the ratio of polymer to metal is from about 1:100 to about 100:1. In another embodiment, the ratio of polymer to metal is from about 1:50 to about 50:1. In another embodiment, the ratio of polymer to metal is from about 1:10 to about 50:1. In another embodiment, the ratio of polymer to metal is from about 1:1 to about 35:1. In another embodiment, the ratio of polymer to metal is from about 1:1 to about 20:1. In another embodiment, the ratio of polymer to metal is from about 10:1 to about 20:1. In another embodiment, the ratio of polymer to metal is from about 12:1 to about 16:1. In one embodiment, the ratio of polymer to metal is about 15:1. Here as elsewhere in the specification and claims, numerical values may be combined to form new or nondisclosed ranges.

Synthesis of Metal-containing Polymer Matrix

The metal-containing polymer matrix may be formed by reducing a metal complex in solution to form metal nanoparticles, metal oxide nanoparticles, or metal sulfide nanoparticles. In one embodiment, the solution for reducing the metal complex also serves as the polymer material for forming the polymer matrix. In one embodiment, the solution for reducing the metal complex is a silicon hydride containing polyorganohydrosiloxane. Non-limiting examples of suitable polyorganohydrosiloxane materials can be those described above.

In one embodiment, the method for forming the metal-containing polymer matrix comprises reacting a metal complex with a silicon hydride containing polyorganohydrosiloxane solution in a suitable solvent to form a colloidal suspension of metal nanoparticles and subsequently reacting the suspension to form a polymer matrix. The reaction may be carried out in an inert atmosphere, such as under a nitrogen atmosphere, to form the metal nanoparticles. In one embodiment, the reaction to form the metal nanoparticles is carried out at a temperature of about 80° C. Following formation of the nanoparticles, the suspension is subjected to an oxygen environment to effect polymerization and encapsulate the metal nanoparticles. The reaction in the presence of oxygen can be carried out for a period of from about 5 to about 40 minutes, in one embodiment from about 10 to about 30 minutes, in another embodiment, from about 15 to about 25 minutes.

The method can also comprise removing an amount of solvent from the colloidal suspension prior to the polymerization/encapsulation reaction. In one embodiment, at least about 50% of the initial solvent content is removed; in another embodiment at least about 60% of the initial solvent content is removed; in another embodiment, at least about 70% of the initial solvent content is removed; in another embodiment, at least about 80% of the initial solvent content is removed. In one embodiment, about 50% to about 100% of the initial solvent content is removed; in another embodiment about 60% to about 100% of the initial solvent content is removed; in another embodiment, about 70% to about 100% of the initial solvent content is removed; in another embodiment about 80% to about 100% of the initial solvent content is removed The metal complex for forming the metal nanoparticles can be a metal compound suitable for providing the desired metal. The metal complex can be a metal compound comprising a metal chosen from aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, or a combination of two or more thereof. Examples of suitable metal complexes for forming metal nanoparticles include, but are not limited to, $PtCl_2$, $H_2PtCl_6$, $Pt_2(dba)_3$, $Pt_2(dvs)_3$, $Pt(OAc)_2 Pt(acac)_2$, $Na_2PtCl_6$, $K_2PtCl_6$, platinum carbonate, platinum nitrate, 1,5-cyclooctadienedimethylplatinum(II), platinum perchlorate, amine complexes of the platinum, ammonium hexachloropalladate(IV), palladium(II) chloride, $AuCl_3$, $Au_2O_3$, $NaAuO_2$, $AgCl$, $AgNO_3$, $CuSO_4$, $CuO$, $Cu(NO_3)_2$, $CuCl_2$, $Ru_2O_3$, $RuCl_2$, $FeCl_2 \cdot 6H_2O$, $ZnCl_2$, $CoCl_2 \cdot 6H_2O$, $NiCl_2 \cdot 6H_2O$, $MnCl_2 \cdot 4H_2O$, $TiCl_4$, vanadium chloride, cadmium chloride, calcium chloride, zirconium tetrachloride, mercuric chloride complexes. As used herein, "dba" refers to dibenzylideneacetone, "dvs" refers to divinyl tetramethyl disiloxane, "OAc" refers to acetate anion, and "acac" refers to acetylacetone ligand.

Support Material

The support material can be selected as desired for a particular purpose or intended use. In one embodiment, the support material can be organic polymer material, an inorganic material, etc. Examples of suitable support materials include, but are not limited to, silicon, silicates such as sodium silicates, borosilicates or calcium aluminum silicates, different types of clay, silica, starch, carbon, alumina, titania, calcium carbonate, barium carbonate, zirconia, metal oxide carbon, nanotubes, synthetic and natural zeolites, polymeric resins in bead or fibrous form, or mixtures of two or more thereof. Examples of suitable organic materials include, polymers containing unsaturated functional groups such as styrene or vinyl containing compounds. Other examples of suitable organic resins include sulfonate resins such as Nafion® resin available from DuPont.

The support material can generally be provided as particles. In one embodiment, the support particles have a particle size of from about 50 to about 1000 micrometers. In one embodiment, the support particles have a particle size of from about 100 to about 800 micrometers. In one embodiment, the support particles have a particle size of from about 200 to about 700 micrometers. In one embodiment, the support particles have a particle size of from about 300 to about 600 micrometers. Here as elsewhere in the specification and claims, numerical values may be combined to form new or nondisclosed ranges. The particle size of the support particles may be determined by any suitable method. In one embodiment, particle size is determined by scanning electron microscopy (SEM).

The support material comprises a functional group attached thereto that is capable of reacting with a moiety of the polymer matrix such that the metal-containing polymer matrix is chemically bonded to the support material. It will be appreciated that the functional group can be provided by the natural surface characteristics of the particles (e.g., surface OH groups on silica) or the particles may be functionalized with a selected moiety to provide a desired reactive site or reactivity. In one embodiment, where the polymer matrix contains a hydrosilane (SiH) moiety, the support material can be functionalized with any group that can react with the SiH moiety such as, for example, via a hydrosilylation reaction, a condensation reaction, etc. In one embodiment, the support material can be modified with a compound comprising a functional group chosen from a group such as silanol, alkoxy, acetoxy, silazane, oximinofunctional silyl group, hydroxyl, acyloxy, ketoximino, amine, aminoxy, alkylamide, hydrogen, allyl or other aliphatic olefinic group, aryl, hydrosulfide, a combination of two or more thereof etc. Silanol, alkoxy, and acetoxy groups are all capable of condensing with Si—H groups. In one embodiment, the support material comprises a functional group having an unsaturated carbon-carbon bond (e.g., a double bond or a triple bond). In one embodiment, the support material has a functional group chosen from —Si—CH=CH$_2$, —Si—OH, —Si—(CH$_2$)$_n$C≡CH, —Si—(CH$_2$)$_n$—NH$_2$, —Si—(CH$_2$)$_n$—OH, —Si—(CH$_2$)$_n$—SH, a combination of two or more thereof, etc, and n 1-26, 1-10, even 1-8. The functional groups provided on the support material can be chosen as desired to facilitate bonding with the functional groups provided on the polymer matrix of the metal-containing matrix material to bond or anchor the metal-containing polymer matrix to the support.

In the case of silica support particles and a metal-containing polymer matrix comprising a hydrosiloxane polymer, the inventors have found that it may be beneficial to functionalize the silica particles with a hydrophobic group to facilitate reaction with the hydrophobic siloxane polymer. In the present invention, this specific functionalization process (i.e., treating the material with a hydrophobic group) is referred to as "capping."

In one embodiment, the substrate particle is functionalized with a silazane. The silazane compound is a generic name of a compound having a Si—N bond in its molecule. Suitable silazanes include, but are not limited to, disilazanes such as alkyldisilazanes. Specific examples of suitable silazanes include, but are not limited to, dimethyl disilazane, trimethyl disilazane, tetramethyl disilazane, pentamethyl disilazane, hexamethyl disilazane (HMDZ), octamethyl trisilazane, hexamethylcyclo trisilazane, tetraethyltetramethylcyclo tetrasilazane, tetraphenyldimethyl disilazane, dipropyltetramethyl disilazane, dibutyltetramethyl disilazane, dihexyltetramethyl disilazane, dioctyltetramethyl disilazane, diphenyl tetramethyl disilazane, and octamethylcyclo tetrasilazane. In addition, a fluorine-containing organic silazane compound obtained by substituting a silazane compound partially with fluorine may be used. In still other embodiments, the silazane compounds comprise carbon-carbon double bonds such as, for example, vinyl groups. An example of a suitable vinyl-containing silazane is divinyltetramethylsilazane (DVTMDZ). Other vinyl-containing compounds useful in the process are vinyltriacetoxysilane and vinyltrialkoxysilanes such as vinyl trimethoxysilane, vinyltriethoxysilane, and vilytriisoproxysilanes.

In one embodiment, the functionalized substrates comprise a combination of alkyldisilazanes and vinyl-containing disilazanes. The ratio of alkyldisilazane to vinyl-containing disilazane can be from about 1000:1 to about 1:1000. In one embodiment, the ratio of alkyldisilazane to vinyl-containing disilazane can be from about 500:1 to about 1:500. In another embodiment, the ratio of alkyldisilazane to vinyl-containing disilazane can be from about 100:1 to about 1:100. In still another embodiment, the ratio of alkyldisilazane to vinyl-containing disilazane can be from about 10:1 to about 1:10. Here as elsewhere in the specification and claims, numerical values can be combined to form new and non-disclosed ranges. In one embodiment, the substrates are functionalized with both hexamethyldisilazane and divinyltetramethylsilazane.

Metal Catalyst Material

The metal catalyst compositions comprise a metal-containing polymer matrix material attached to the (functionalized) substrate particles. The metal-containing polymer matrix material can be formed by reacting the metal-containing polymer matrix material and the substrate under conditions sufficient to bond the polymer matrix material to the functional groups on the substrates. In one embodiment, the metal-containing polymer matrix comprises a polyhydrosiloxane comprising SiH groups, and the SiH groups react with the functional groups disposed on the substrate material. FIG. 1 is a schematic illustrating a scheme 10 for forming catalyst materials in accordance with aspects of the present invention. As shown in FIG. 1, a polymer material 20 (illustrated as PMHS in FIG. 1) is reacted with a metal complex (e.g., a platinum complex) to provide a metal-containing polymer matrix 30 comprising nanoparticles 32 encapsulated in the matrix. The metal-containing polymer matrix 30 is reacted with a support material 40 (e.g., functionalized silica particles) to provide a catalyst material 50 comprising the metal-containing polymer matrix bonded to the support material.

The reaction of the polymer functional moieties with the functional groups attached to the substrate can be carried out by any suitable means depending on the moieties undergoing reaction. For example, the reaction may be carried out in the presence or absence of a solvent as desired. In one embodiment the reaction is carried out at a temperature of from about 5° C. and 150° C. In one embodiment, the reaction is carried out at a pressure ranging from about 0.001 to about 10 bar.

The metal loading concentration in the metal catalyst material can be from about 0.001 to about 20 percent by weight based on the total weight of the substrate particles. In one embodiment, the metal loading concentration in the metal catalyst material can be from about 0.01 to about 15 percent by weight based on the total weight of the substrate particles. In another embodiment, the metal loading concentration in the metal catalyst material may be from about 0.05 to about 5 percent by weight based on the total weight of the substrate particles. In still another embodiment, the metal loading concentration in the metal catalyst material may be from about 0.1 to about 1 percent by weight based on the total weight of the substrate particles.

The metal catalysts can be employed as catalysts for a wide variety of reactions including, but not limited to hydrosilylation, hydroxylation, silaesterification, hydrogenation, oxidation, Heck and Suzuki coupling, dehydrocoupling or any other metal catalyzed reaction now known or developed in the future. The present invention is particularly suitable in a hydrosilylation process comprising contacting a silicon hydride with an unsaturated reactant in the presence of a metal catalyst. Silicon hydrides useful in the present process can be a polymer described by the general formula (1) or a monomer having a general formula $R'_m H_n SiX_{4-m-n}$, where each R' is independently selected from the group consisting of alkyls comprising one to 20 carbon atoms, cycloalkyls comprising four to 12 carbon atoms, and aryls; m=0 to 3, n=1 to 3, and m+n=1 to 4. R' can be a substituted or unsubstituted alkyl, cycloalkyl, or aryl as described. Each X is independently selected from the group consisting of OR' and halides. Examples, of silicon hydrides that can be useful in the present process include, but are not limited to, triethoxysilane, trimethoxysilane, trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane and (3,3,3-trifluoropropyl) dichlorosilane. The unsaturated reactant of the present invention is a hydrocarbon compound or an unsaturated polyether. The hydrocarbon compound can be described by, for example, formulas $(CH_2=CH(CH_2)_g)_h R'_i Si(OR')_{4-h-i}$ and $(CH_2=CH(CH_2)_g R'_i SiCl_{4-h-i}$, where R' is as previously described, g=0 to 20, h=1 to 3, i=0 to 3, and h+i=1 to 4. The unsaturated hydrocarbon compounds may also comprise 1-hexene and 1-5 hexadiene, trans-2-hexene, styrene, alpha-methylstyrene, eugenol, 1-octene, allyl glycidylether, trivinylcyclohexane, allylmethoxytriglycol, allylmethacrylate, allylamine, trichloroethylene, allyl and vinyl ethers and dichlorostyrene. The unsaturated polyethers of this invention are blocked or random polyoxyalkylenes having the general formula (X), (Y), or (Z):

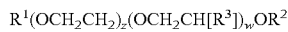

$R^1(OCH_2CH_2)_z(OCH_2CH[R^3])_w OR^2$     (X);

$R^2O(CH[R^3]CH_2O)_w(CH_2CH_2O)_z CR^4{}_2C\equiv CCR^4{}_2$
$(OCH_2CH_2)_z(OCH_2CH[R^3])_w R^2$     (Y);

or

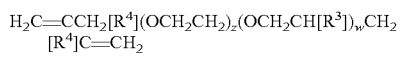

$H_2C=CCH_2[R^4](OCH_2CH_2)_z(OCH_2CH[R^3])_w CH_2$
$[R^4]C=CH_2$     (Z)

In the formulas, $R^1$ denotes an unsaturated organic group containing from 3 to 10 carbon atoms such as allyl, methallyl, propargyl, or 3-pentynyl. When the unsaturation is olefinic, it is desirably terminal to facilitate smooth hydrosilylation. However, when the unsaturation is a triple bond it may be internal. $R^2$ is hydrogen, or a polyether capping group of from 1 to 8 carbon atoms such as alkyl groups (e.g., $CH_3$, n-$C_4H_9$ or i-$C_8H_{17}$), acyl groups (e.g., $CH_3COO$—, t-$C_4H_9$ COO), beta-ketoester group (e.g., $CH_3C(O)CH_2C(O)O$—), or a trialkylsilyl group. $R^3$ and $R^4$ are monovalent hydrocarbon groups such as $C_1$-$C_{20}$ alkyl group (e.g., methyl, ethyl, isopropyl, 2-ethylhexyl, dodecyl and stearyl), or aryl groups (e.g., phenyl and naphthyl), or alkaryl groups (e.g., benzyl, phenylethyl and nonylphenly), or cycloalkyl groups (e.g., cyclohexyl and cyclooctyl). $R^4$ can also be hydrogen. In one embodiment, the $R^3$ and/or $R^4$ groups are methyl. The subscript z is 0 to 100 inclusive, and w is 0 to 100 inclusive, but z+w>0. In one embodiment, the values of z and w are 1 to 50 inclusive.

The catalysts exhibit excellent activity and can provide high conversion rates in a shorter time period compared to other heterogeneous metal catalysts. Additionally, the catalysts can be recovered by simple filtration techniques and reused to catalyze a reaction. In one embodiment, the catalysts can be reused at least 5 times and exhibit excellent catalytic activity, even comparable or substantially the same as the catalytic activity for the first use of the catalyst. In one embodiment, the catalyst can be used at least 7 times, at least 8 times, even at least 10 times and still exhibit excellent catalytic activity. In one embodiment, the catalytic activity of the catalyst after a first, second, third, fourth, or fifth reuse is substantially similar to the catalytic activity of the catalyst the first time the catalyst is used. In one embodiment, the catalyst has a catalytic activity the same as or at least 85%, 90%, 95%, 99%, 99.9%, 99.99% or even at least about 99.999% of the catalytic activity of the catalyst used to conduct a prior reaction. As used herein the catalytic activity can be evaluated by or refer to the percent conversion or the rate of reaction for a particular reaction.

The catalysts of the present invention may be used in a batch, semi batch, or continuous mode at temperatures between −20° C. and 500° C., −10° C. to about 250° C., about 0° C. to about 200° C., even about 5° C. to about 150° C. The catalysts can be formed at pressures of from about 0.001 to about 100 bar, in one embodiment at a pressure from 0.001 bar to about 10 bar. A stirred bed reactor may be run under batch, semi-batch and continuous conditions. In contrast, a fixed bed reactor is typically run under continuous conditions.

While the invention has been described with respect to various embodiments, aspects of the invention may be further understood in view of the following examples. The examples are for illustrating aspects of the invention and are not intended to limit the invention.

EXAMPLES

Example 1

Modification of Silica Surface

A mixture of 15 g of silica gel procured from Sigma-Aldrich, 4 g of Hexamethyldisilazane (HMDZ), and 0.2 g of Divinyltetramethyldisilazane (DVTMDZ) are added into a 500 ml round bottom flask. The round bottom flask is equipped with a magnetic stirrer, reflux condenser and a thermometer. To the above reactant solution, 4 g of water and 100 g of isopropyl alcohol (IPA) are added. The temperature of the reaction is maintained in between 70-80° C. The reaction is continued under stirring for 4 hours. After cooling, the solution is decanted off and dried at 65° C. for 3 hours in a drying oven. This gives a silica powder having hydrophobic vinyl groups on the silica surface.

Example 2

Synthesis of Uncapped Pt/SiO$_2$ Catalyst

A mixture of 42 mg of Pt complex (cyclooctadienemethylplatinum(II) (0.012 mmol, 42 mg), polymethylhydrosiloxane (0.182 mmol, 600 mg, Mw 3300), and 25 ml toluene solution are added in a 100 ml 3-necked round bottom flask. Polymethylhydrosiloxane (PMHS) acts as both the reducing and stabilizing agent. The round bottom flask is equipped with a magnetic stirrer, reflux condenser and a thermometer. The flask is in continuous supply of dry nitrogen gas. The reaction mixture is subsequently heated to 80° C. for 24 hours to form Pt metal atoms from Pt ions via chemical reduction process using the PMHS polymer. After 24 hours, the color of the solution changed from white to a dark yellowish color, which indicates that colloidal particles of Pt are formed in the process. Furthermore, the disappearance of the absorption peak (wavelength=319.0 nm) for metal ions in the UV spectrum also suggests that Pt nano metal particles are formed in the solution. After confirming Pt nano-particle formation by UV spectroscopy, nitrogen flow is stopped and flow of oxygen (2 ml/min) is started into the round bottom flask to promote cross-linking of the PMHS polymer and to encapsulate the Pt nano-particles in a cross-linked PMHS matrix. The stabilization of Pt nano-particles in a cross-linked PMHS matrix is continued for 15 mins. The PMHS stabilized Pt nano-particles (taken out from flask) and 7.5 g of vinyl functionalized silica (particle size: 100-200 mesh size or 80-100 μm) from example 1 are transferred into a petri dish and mixed thoroughly to form a homogeneous catalyst powder. This catalyst is then further dried in an oven for 3 hrs to remove any volatile contents. This gives an uncapped $Pt/SiO_2$ catalyst powder having a Pt content of 0.2% by weight.

Example 3

Synthesis of Capped $Pt/SiO_2$ Catalyst

A mixture of 5 g of uncapped catalyst from Example 2, 1.66 g of hexamethyldisilazane (HMDZ), and 4 g of water are added into a 250 ml round bottom flask. The round bottom flask is equipped with a magnetic stirrer, reflux condenser and a thermometer. To the above reactant solution 50 g of isopropanol (IPA) is added. The temperature of the reaction is maintained in between 70-80° C. The reaction is continued under stirring for 4 hours. After cooling, the solution is decanted off and dried at 65° C. for 3 hours in a drying oven. This gives a capped $Pt/SiO_2$ catalyst powder having a Pt content of 0.2% by weight.

Figure 2B:
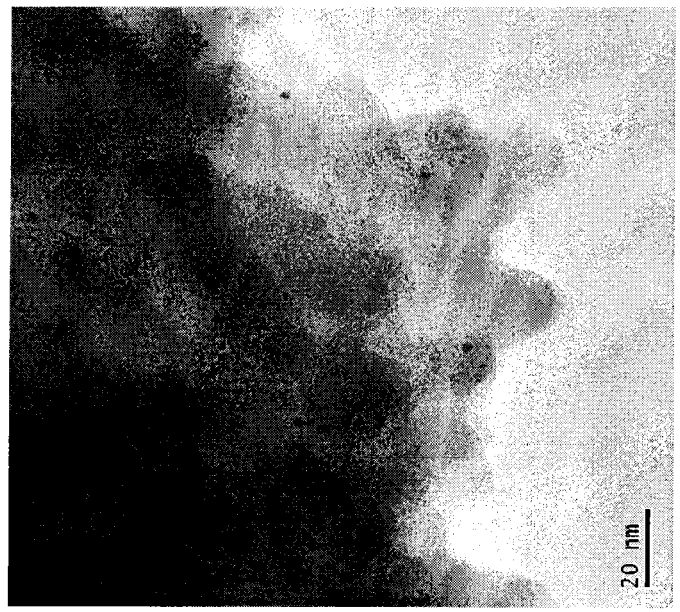
FIGS. 2a and 2b shows TEM images of Pt nanoparticles supported on silica.
Figure 2A:
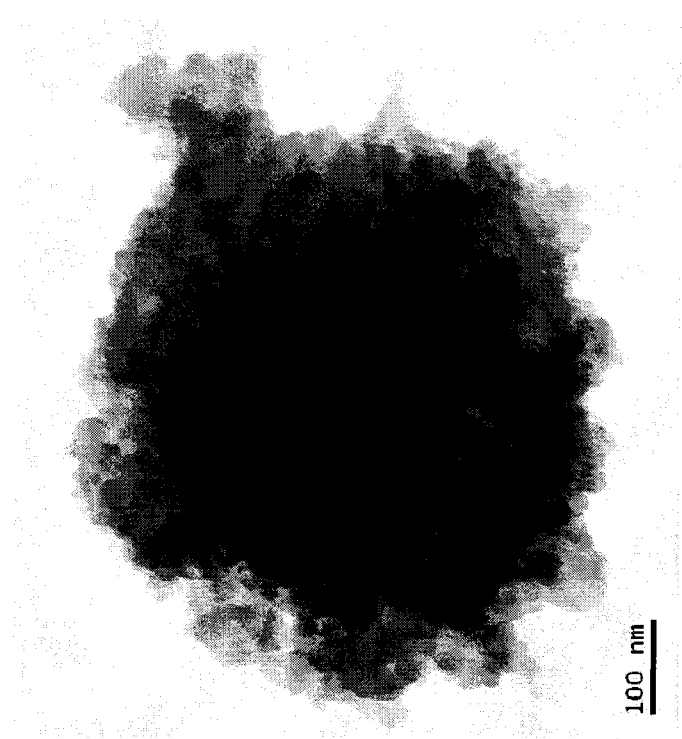

FIG. 2a shows a TEM (transmission electron microscopy) image of the capped $Pt/SiO_2$ catalyst taken at 135,000 magnification. FIG. 2b shows a TEM image of the capped $Pt/SiO_2$ catalyst prepared by a method described in Example 3 taken at 650,000 magnification. From the image in FIG. 2b, it is shown that platinum nanoparticles with a size of 1-5 nm are uniformly dispersed in a cross-linked siloxane network on the catalyst surface.

Figure 3:
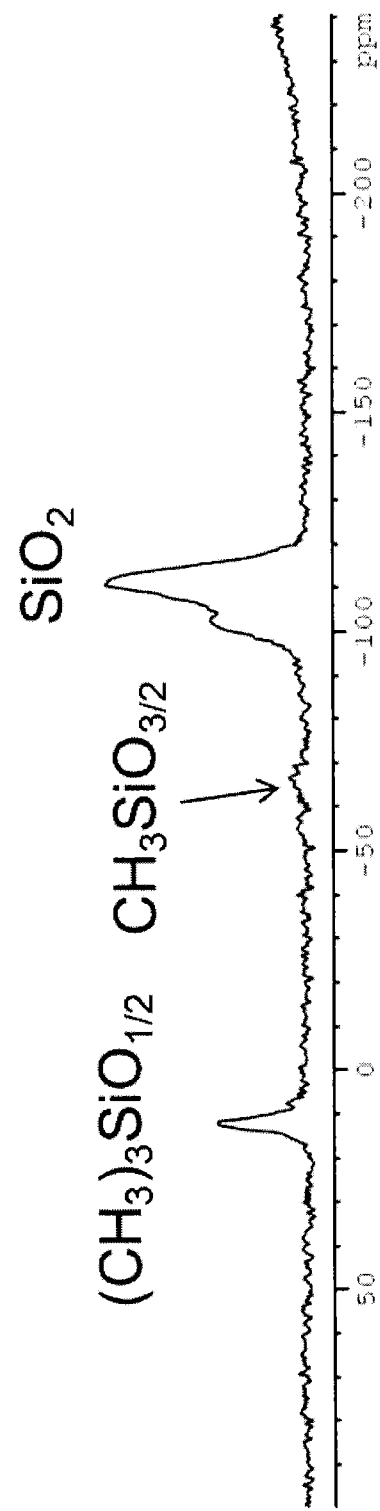
FIG. 3 is a solid state $^{29}$Si NMR spectrum of a metal catalyst in accordance with one embodiment of the invention.
Figure 4:
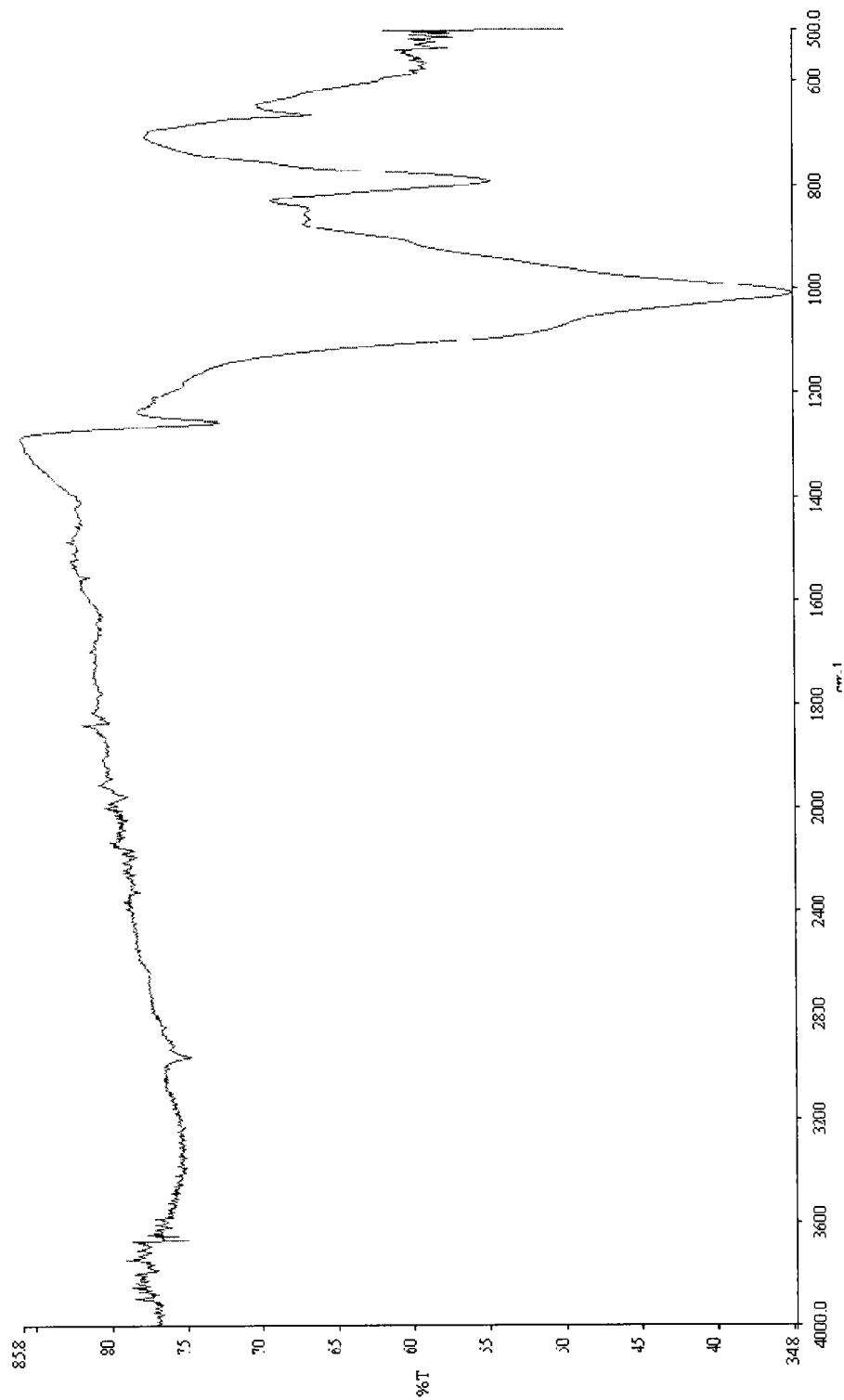
FIG. 4 is an FTIR spectrum of a metal catalyst in accordance with one embodiment of the invention.

FIG. 3 is a CP/MAS solid state $^{29}Si$ NMR spectrum of the capped $Pt/SiO_2$ catalyst prepared by a method described in Example 3 and shows the presence of cross-linked siloxane network $(CH_3SiO_{3/2})$ and trimethylsiloxane $[(CH_3)_3SiO_{1/2}]$ moieties onto the silica $(SiO_2)$ support. The presence of these moieties was further documented by FTIR spectroscopy, which showed characteristic signals associated with Si—O—Si and Si—$CH_3$ bonds. FIG. 4 shows the results of analysis of capped $Pt/SiO_2$ catalyst by FTIR spectroscopy. As shown in FIG. 4, the disappearance of Si—H and Si-vinyl groups confirms that the residual Si—H groups of condensed siloxane polymer (contains encapsulated Pt nano-particles) are reacted with vinyl groups of silica surface via hydrosilylation reaction.

Examples 4-16

Reactions Employing Catalyst Compositions

The catalysts of Examples 2 and 3 are utilized in various reactions described in Examples 4-16.

Example 4

The hydrosilylation of 1-octene and heptamethyltrisiloxane hydride is evaluated in the presence of a 0.2% $Pt/SiO_2$ catalyst prepared by a method similar to method for preparing $Pt/SiO_2$ catalyst described in Example 2. The hydrosilylation experiments are conducted in a 3-necked round bottom flask. The round bottom flask is equipped with a magnetic stirrer, reflux condenser and a thermometer. 1-octene (0.1651 mol, 18.5 grams) and heptamethyltrisiloxane hydride (0.1324 mol, 29.4 grams) are added into the round bottom flask and the temperature is maintained at 120° C. The catalyst (20 ppm of Pt metal) is added to the reaction mixture at 120° C., and the moment of this addition is marked as the beginning of the reaction. Disappearance of starting materials and formation of products are recorded by $^1HNMR$. The reaction temperature, reaction time, and conversion of heptamethylhydrosiloxane hydride and yield of the hydrosilylated product are reported in Table 1.

TABLE 1

| | | | Reaction Conditions | | | | |
|---|---|---|---|---|---|---|---|
| | | | Temp | Pt Loading | | % Conversion | % Hydrosilylated |
| | | Reactants | | | | | |
| Example | Olefin | SiH | (° C.) | (ppm) | Time | of Si—H | Product |
| 4 | 1-octene | Heptamethyltrisiloxane hydride | 80-90 | 20 | 2 hrs | 98 | 98 |
| 7 | Allylglycidylether | Heptamethyltrisiloxane hydride | 120 | 20 | 5.5 hrs | 30 | 30 |
| 8 | Polyalkyleneoxide polymer | Heptamethyltrisiloxane hydride | 120 | 20 | 8.5 hrs | 75 | 75 |
| 9 | Eugenol | Hydrogen terminated polysiloxane hydride | 120 | 10 | 12 mins | 99 | 99 |
| 10 | Allylmethoxytriglycol | Undecamethylpenta siloxane | 120 | 20 | 1 hr | 70 | 70 |
| 11 | 1-octene | Triethoxy silane | 120 | 400 | 4 hr | 8 | 8 |

Example 5

The reuse potential of the 0.2% Pt/SiO$_2$ (synthesized catalyst prepared by a method described in Example 2) in the hydrosilylation of 1-octene and heptamethyltrisiloxane hydride is evaluated. The experiment is repeated using the same procedure described in Example 4. After the completion of reaction, the catalyst is recovered by simple filtration and recharged with fresh reactants, and reused in the next reaction. Results of reuse test are reported in Table 2. From Table 2, it is clear that the synthesized Pt/SiO$_2$ catalyst can be reused up to five times without any loss of catalytic activity. Table 2 clearly suggests that a minimum amount of Pt (<0.2 ppm) was leached into the product samples.

TABLE 2

| | Reaction Conditions | | | | |
|---|---|---|---|---|---|
| Experiment | Temp (° C.) | Pt Loading (ppm) | Time | % Hydrosilylated product | Leached Pt amount (ppm) |
| Use 1 | 80-90 | 20 | 2 hrs | 98 | 0.18 |
| Reuse 2 | 80-90 | 20 | 2 hrs | 97 | 0.005 |
| Reuse 5 | 80-90 | 20 | 2 hrs | 98 | 0.001 |

Example 6

Evaluation of the hydrosilylation of 1-octene and heptamethyltrisiloxane hydride in the presence of 0.2% Pt/SiO$_2$ catalyst prepared by a method similar to method for preparing Pt/SiO$_2$ catalyst described in Example 2 except that different mole ratios of the polymethylhydrosiloxane to Pt complex ratios are used. The experiment is repeated using the same procedure described in Example 4. The mole ratios of PMHS to Pt complex, reaction time and conversion of heptamethylhydrosiloxane hydride and yield of the hydrosilylated product are reported in Table 3. As shown in Table 3, a ratio of PMHS polymer to Pt complex (cyclooctadienedimethylplatinum(II)) of 15:1 illustrates an exemplary embodiment for achieving both high activity and reduced Pt leaching.

TABLE 3

| Mole ratio of PHMS:Pt complex | Reaction time | % Conversion of Si—H | % Hydrosilylated product | Leached Pt amount (ppm) |
|---|---|---|---|---|
| 15:1 | 2 hrs | 98 | 98 | 0.18 |
| 10:1 | 1 hr | 98 | 98 | >5 |
| 20::1 | 3 hrs | 80 | 80 | 0.18 |

Example 7

Evaluation of the hydrosilylation of allylglycidylether and heptamethyltrisiloxane hydride in the presence of 0.2% Pt/SiO$_2$ catalyst prepared by a method similar to method for preparing Pt/SiO$_2$ catalyst described in Example 2. The hydrosilylation experiments are conducted in a 3-necked round bottom flask. The round bottom flask is equipped with a magnetic stirrer, reflux condenser and a thermometer. Allylglycidylether (0.04 mol. 10 grams) and heptamethyltrisiloxane hydride (0.075 mol, 16.9 grams) are added into the round bottom flask and the temperature is maintained at 120° C. The catalyst (20 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time and conversion of heptamethylhydrosiloxane hydride are reported in Table 1.

Example 8

Evaluation of the hydrosilylation of methoxy terminated allylplyethyleneoxide (Mw~350) and heptamethyltrisiloxane hydride in the presence of 0.2% Pt/SiO$_2$ catalyst prepared by a method similar to method for preparing Pt/SiO$_2$ catalyst described in Example 2. The hydrosilylation experiments are conducted in a 3-necked round bottom flask. The round bottom flask is equipped with a magnetic stirrer, reflux condenser and a thermometer. Polyalkyleneoxide polymer (0.0571 mol, 20 grams) and heptamethyltrisiloxane hydride (0.0304 mol. 15 grams) are added into the round bottom flask and the temperature is maintained at 120° C. The catalyst (20 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time and conversion of heptamethylhydrosiloxane hydride and yield of the hydrosilylated product are reported in Table 1.

Example 9

Evaluation of the hydrosilylation of eugenol and hydrogen terminated polydimethylsiloxane (Average Mw~3300) in the presence of 0.2% Pt-silica catalyst prepared by a method similar to a method for preparing supported catalyst described in Example 2. The hydrosilylation experiments are conducted in a 3-necked round bottom flask. The round bottom flask is equipped with a magnetic stirrer, reflux condenser and a thermometer. Eugenol (0.0608 mol, 10 grams) and hydrogen terminated disiloxane (0.0288 mol, 95.177 grams) are added into the round bottom flask and the temperature is maintained at 120° C. The catalyst (10 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time and conversion of hydrogen terminated polydimethylsiloxane and yield of the hydrosilylated product are reported in Table 1.

Example 10

Evaluation of the hydrosilylation of allylmethoxytriglycol and undecamethylpentasiloxane [Me$_3$SiO(Me$_2$SiO)$_2$(MeHSiO)SiMe$_3$] (as used herein, "Me" refers to methyl group) in the presence of 0.2% Pt-silica catalyst prepared by a method similar to a method for preparing supported catalyst described in Example 2. The hydrosilylation experiments are conducted in a 3-necked round bottom flask. The round bottom flask is equipped with a magnetic stirrer, reflux condenser and a thermometer. Allylmethoxytriglycol (0.048 mol, 10 grams) and undecamethylpentasiloxane (0.0303 mol, 11.3 grams) are added into the round bottom flask and the temperature is maintained at 120° C. The catalyst (20 ppm of Pt metal) is added to the reaction mixture of at 120° C., and the moment of this addition is marked as the beginning of the reaction. Disappearance of starting materials and formation of products are recorded by $^1$HNMR. The reaction temperature, and conversion of undecamethylpentasiloxane and yield of the hydrosilylated product are reported in Table 1.

Example 11

Evaluation of the hydrosilylation of 1-octene and triethoxysilane in the presence of 0.2% Pt-silica catalyst prepared by a method similar to a method for preparing supported catalyst described in Example 2. The hydrosilylation experiments are conducted in a 3-necked round bottom flask. The round bottom flask is equipped with a magnetic stirrer, reflux condenser and a thermometer. 1-octene (0.091 mol, 10.2 grams) and triethoxysilane (0.078 mol, 12.6 grams) are added into the round bottom flask and the temperature is maintained at 120° C. The catalyst (400 ppm of Pt metal) is added to the reaction mixture at 120° C., and the moment of this addition is marked as the beginning of the reaction. Disappearance of starting materials and formation of products are recorded by $^1$HNMR. The reaction temperature, total conversion of triethoxysilane and yield of the hydrosilylated product are reported in Table 1.

Example 12

Evaluation of the hydrosilylation of 1-octene and heptamethyltrisiloxane hydride in the presence of 0.2% Pt/SiO$_2$ catalyst prepared by a method similar to method for preparing Pt/SiO$_2$ catalyst described in Example 3. The hydrosilylation experiments are conducted in a 3-necked round bottom flask. The round bottom flask is equipped with a magnetic stirrer, reflux condenser and a thermometer. 1-octene (0.1651 mol, 18.5 grams) and heptamethyltrisiloxane hydride (0.1324 mol, 29.4 grams) are added into the round bottom flask and the temperature is maintained at 120° C. The catalyst (20 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time and conversion of heptamethylhydrosiloxane hydride and yield of the hydrosilylated product are reported in Table 4.

Example 13

Evaluation of the hydrosilylation of allylglycidylether and heptamethyltrisiloxane hydride in the presence of 0.2% Pt/SiO$_2$ catalyst prepared by a method similar to method for preparing Pt/SiO$_2$ catalyst described in Example 3. The hydrosilylation experiments are conducted in a 3-necked round bottom flask. The round bottom flask is equipped with a magnetic stirrer, reflux condenser and a thermometer. Allylglycidylether (0.04 mol, 10 grams) and heptamethyltrisiloxane hydride (0.075 mol, 16.9 grams) are added into the round bottom flask and the temperature was maintained at 120° C. The catalyst (20 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time, conversion of heptamethylhydrosiloxane hydride and yield of the hydrosilylated product are reported in Table 4.

Example 14

Evaluation of the hydrosilylation of methoxy terminated allylpolyethyleneoxide (Mw~350) polymer and heptamethyltrisiloxane hydride in the presence of 0.2% Pt/SiO$_2$ catalyst prepared by a method similar to method for preparing Pt/SiO$_2$ catalyst described in Example 3. The hydrosilylation experiments are conducted in a 3-necked round bottom flask. The round bottom flask is equipped with a magnetic stirrer, reflux condenser and a thermometer. Polyalkyleneoxide polymer (0.0571 mol, 20 grams) and heptamethyltrisiloxane hydride (0.0304 mol, 10.66 grams) were added into the round bottom flask and the temperature is maintained at 120° C. The catalyst (20 ppm of Pt metal) is added to the reaction mixture of at 120° C., and the moment of this addition is marked as the beginning of the reaction. Disappearance of starting materials and formation of products are recorded by $^1$HNMR. The reaction temperature, reaction time and conversion of heptamethylhydrosiloxane hydride and yield of the hydrosilylated product are reported in Table 4.

Example 15

Evaluation of the hydrosilylation of eugenol and hydrogen terminated polydimethylsiloxane (Average Mw ~3300) in the presence of 0.2% Pt-silica catalyst prepared by a method similar to a method for preparing supported catalyst described in Example 3. The hydrosilylation experiments are conducted in a 3-necked round bottom flask. The round bottom flask is equipped with a magnetic stirrer, reflux condenser and a thermometer. Eugenol (0.0608 mol, 10 grams) and hydrogen terminated disiloxane (0.0288 mol, 95.177 grams) are added into the round bottom flask and the temperature is maintained at 120° C. The catalyst (10 ppm of Pt metal) is added to the reaction mixture at 120° C., and the moment of this addition is marked as the beginning of the reaction. Disappearance of starting materials and formation of products are recorded by $^1$HNMR. The reaction temperature, reaction time and conversion of hydrogen terminated polydimethylsiloxane and yield of the hydrosilylated product are reported in Table 4.

Example 16

Evaluation of the hydrosilylation of 1-octene and triethoxysilane in the presence of 0.2% Pt-silica catalyst prepared by a method similar to a method for preparing supported catalyst described in Example 3. The hydrosilylation experiments are conducted in a 3-necked round bottom flask. The round bottom flask is equipped with a magnetic stirrer, reflux condenser and a thermometer. 1-octene (0.091 mol, 10.2 grams) and triethoxysilane (0.078 mol, 12.6 grams) are added into the round bottom flask and the temperature is maintained at 120° C. The catalyst (20 ppm of Pt metal) is added to the reaction mixture at 120° C., and the moment of this addition is marked as the beginning of the reaction. Disappearance of starting materials and formation of products are recorded by $^1$HNMR. The reaction temperature, total conversion of triethoxysilane, and % yield of the hydrosilylated product are reported in Table 4.

TABLE 4

| | Reactants | | Reaction Conditions | | | | % Hydrosilylated Product |
|---|---|---|---|---|---|---|---|
| Ex. | Olefin | SiH | Temp (° C.) | Pt Loading (ppm) | Time | % Conv. of Si—H | |
| 12 | 1-octene | HMTS | 80-90 | 20 | 2 hrs | 98 | 98 |
| 13 | AGE | HMTS hydride | 120 | 20 | 2.5 hrs | 98 | 98 |
| 14 | PAO polymer | HMTS hydride | 120 | 20 | 1 hr | 80 | 80 |
| 15 | Eugenol | H-terminated polydimethyl siloxane | 120 | 10 | 12 mins | 99 | 99 |
| 16 | 1-octene | Triethoxysilane | 120 | 20 | 45 mins | 98 | 60 |

AGE = Allylglycidylether
PAO = Polyalkyleneoxide
HMTS = Heptamethyltrisiloxane

Comparison to Conventional Catalysts

The catalytic activity of a synthesized Pt/SiO$_2$ catalyst prepared by a method described in Example 3 is compared with that of a catalyst made with traditional methods (a 3.6% Pt metal (500 nm) deposited on silica available from JM as 3.6R210, 3.6% platinum on silica catalyst and designated as "Commercial" in Table 5) for various hydrosilylation reactions in accordance with Examples 11-15. The results of the experiment are shown in Table 5.

TABLE 5

| Reaction Example | Catalyst type | Time | % Conversion of Si—H | % Hydrosilylated product |
|---|---|---|---|---|
| 11 | Example 3 | 2 hrs | 98 | 98 |
| 11 | Commercial | 6 hrs | 55 | 55 |
| 12 | Example 3 | 2.5 hrs | 98 | 98 |
| 12 | Commercial | 5.5 hrs | 70 | 70 |
| 13 | Example 3 | 1 hr | 80 | 80 |
| 13 | Commercial | 4.5 hrs | 80 | 80 |
| 14 | Example 3 | 12 mins | 99 | 99 |
| 14 | Commercial | 65 mins | 72.5 | 72.5 |
| 15 | Example 3 | 45 mins | 98 | 60 |
| 15 | Commercial | 4.5 hrs | 9 | 9 |

From Table 5, it is clear that the synthesized Pt/SiO$_2$ catalyst according to the present invention exhibits superior catalytic activity in terms of both the rate of conversion and completeness of the reaction than those of commercial Pt/SiO$_2$ catalyst.

Product samples obtained with (1) a catalyst in accordance with aspects of the present invention, (2) a homogenous catalyst, and (3) a supported nano Pt catalyst were visually compared. The material made with the catalyst in accordance with the present invention is clear (<0.3 ppm of Pt leaching), while the material formed using the other catalysts has a yellowish color (which indicates leaching (>5 ppm) of the platinum into the solution). This result suggests that the instant method our approach of preparing supported nano Pt catalyst is superior in arresting the leaching compared to the conventional techniques of synthesizing a supported nano Pt catalyst.

Other Applications of the Present Catalyst

Example 18

Pt/SiO$_2$ Catalyst for Hydroxylation of Triethylsilane

Hydroxylation of triethylsilane is carried in the presence of 0.2% Pt-silica catalyst prepared by a method similar to a method for preparing supported catalyst described in example 3. A 300 ml round bottom flask is thoroughly flushed with dry nitrogen gas and charged with 0.05 g of 0.2% Pt-silica catalyst. To this solid catalyst, dry tetrahydrofuran (2 ml), a triethylsilane (1.0 mmol) and H$_2$O (2.0 mmol) are added consecutively and the reaction mixture is stirred at room temperature for 5 hours. The triethylsilanol product is analyzed by HNMR.

Example 19

Pt/SiO$_2$ Catalyst for Hydrogenation of Acetylene

Hydrogenation of acetylene is carried in the presence of 0.2% Pt-silica catalyst (synthesized by a method described in example 3) by feeding an initial gas mixture of 9.8 mol % C$_2$H$_2$, 9.5 mol % N$_2$ and 80.7 mol % H$_2$ to the reactor at a flow rate of 1720 ml/min and at atmospheric pressure. Composition of gas streams is measured with gas chromatography, and reported in mol %.

Embodiments of the invention have been described above and, obviously, modifications and alterations will occur to others upon the reading and understanding of this specification. The invention and any claims are intended to include all modifications and alterations insofar as they come within the scope of the claims or the equivalent thereof.

The invention claimed is:

1. A heterogeneous catalyst comprising a metal-containing siloxane polymer matrix covalently bonded to a support material,
   wherein the support material is chosen from silicon, a sodium silicate, a borosilicate, a calcium aluminum silicate, clay, silica, calcium carbonate, barium carbonate, a metal oxide, and mixtures of two or more thereof;
   wherein the support material comprises a functional group chosen from silanol, alkoxy, acetoxy, silazane, oximino-functional silyl group, hydroxyl, acyloxy, ketoximino, amine, aminoxy, alkylamide, hydrogen, an aliphatic olefinic group, aryl, hydrosulfide, or a combination of two or more thereof;
   wherein the metal-containing siloxane polymer matrix comprises metal nanoparticles encapsulated in a siloxane polymer matrix, wherein the polymer matrix comprises a crosslinked or partially crosslinked network of hydrosiloxanes with a vinyl silicone compound, wherein the hydrosiloxanes are chosen from a silicon hydride-containing polyorganohydrosiloxane of the general formula:

$$M^1_a M^2_b D^1_c D^2_d T^1_e T^2_f Q_j$$

wherein: $M^1=R^1R^2R^3SiO_{1/2}$; $M^2=R^4R^5R^6SiO_{1/2}$; $D^1=R^7R^8SiO_{2/2}$; $D^2=R^9R^{10}SiO_{2/2}$; $T^1=R^{11}SiO_{3/2}$; $T^2=R^{12}SiO_{3/2}$; $Q=SiO_{4/2}$; $R^1$, $R^2$, $R^3$, $R^4$, $R^5$, $R^6$, $R^7$, $R^8$, $R^9$, $R^{10}$, $R^{11}$, and $R^{12}$ are aliphatic, aromatic or fluoro monovalent hydrocarbon having from 1 to 60 carbon atoms; at least one of $R^9$ or $R^{12}$ is hydrogen; and the subscript a, b, c, d, e, f, and j are zero or positive subject to the following limitations: $2 \leq a+b+c+d+e+f+j \leq 6000$, and $b+d+f>0$;

wherein the covalent bond is formed between the functional group present on the support material and the siloxane polymer matrix.

2. The catalyst of claim 1, wherein the metal nanoparticles are chosen from nanoparticles of aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, oxides and sulfides of such metal, or combinations of two or more thereof.

3. The catalyst of 1 wherein the metal-containing polymer matrix has a ratio of polymer to metal of from about 1:1000 to about 100:1.

4. The catalyst of claim 1, wherein the metal-containing polymer matrix has a weight ratio of polymer to metal of from about 1:1 to about 20:1.

5. The catalyst of claim 1, wherein the metal-containing polymer matrix has a weight ratio of polymer to metal of from about 10:1 to about 20:1.

6. The catalyst of claim 1, wherein the metal-containing polymer matrix has a weight ratio of polymer to metal of from about 12:1 to about 16:1.

7. The catalyst of claim 1 wherein the metal particles have a particle size of from about 1 to about 100 nanometers.

8. The catalyst of claim 1 wherein the metal loading ranges from about 0.05 to about 5 percent by weight of the support material.

9. The catalyst of claim 1 wherein the metal loading ranges from about 0.1 to about 1 percent by weight of the support material.

10. The catalyst of claim 1, wherein the support material comprises a functional group chosen from —Si—CH=CH$_2$, —Si—OH, —Si—(CH$_2$)$_n$C≡CH, —Si—(CH$_2$)$_n$—NH$_2$, —Si—(CH$_2$)$_n$—OH, —Si—(CH$_2$)$_n$—SH, or a combination of two or more thereof, and n is 1-26.

11. The catalyst of claim 1 wherein the metal-containing polymer matrix is covalently bonded to the support material via a hydrophobic functional group attached to the support material.

12. The catalyst of claim 11 wherein the hydrophobic functional group is chosen from a silazane-containing functional group.

13. A method of synthesizing supported nanoparticle catalysts, the method comprising:
(a) forming a metal-containing polymer matrix comprising metal nanoparticles by forming a colloidal suspension of metal nano-particles by reacting metal complexes with a silicon hydride-containing polyorganohydrosiloxane solution to form a colloidal suspension of metal nano-particles and subsequently reacting the suspension to form a polymer matrix and encapsulate the metal nano-particles in a siloxane matrix, wherein the polymer matrix comprises a crosslinked or partially crosslinked network of hydrosiloxanes with a vinyl silicone compound, and the hydrosiloxanes are chosen from a silicon hydride-containing polyorganohydrosiloxane of the general formula:

$$M^1_a M^2_b D^1_c D^2_d T^1_e T^2_f Q_j$$

wherein: $M^1=R^1R^2R^3SiO_{1/2}$; $M^2=R^4R^5R^6SiO_{1/2}$; $D^1=R^7R^8SiO_{2/2}$; $D^2=R^9R^{10}SiO_{2/2}$; $T^1=R^{11}SiO_{3/2}$; $T^2=R^{12}SiO_{3/2}$; $Q=SiO_{4/2}$; $R^1$, $R^2$, $R^3$, $R^4$, $R^5$, $R^6$, $R^7$, $R^8$, $R^9$, $R^{10}$, $R^{11}$, and $R^{12}$ are aliphatic, aromatic or fluoro monovalent hydrocarbon having from 1 to 60 carbon atoms; at least one of $R^9$ or $R^{12}$ is hydrogen; and the subscript a, b, c, d, e, f, and j are zero or positive subject to the following limitations: $2 \leq a+b+c+d+e+f+j \leq 6000$, and $b+d+f>0$; and (b) attaching the metal-containing polymer matrix to a support material via covalent chemical bonds, wherein the support material is chosen from silicon, a sodium silicate, a borosilicate, a calcium aluminum silicate, clay, silica, metal oxide, and mixtures of two or more thereof; and wherein the support material comprises a functional group chosen from silanol, alkoxy, acetoxy, silazane, oximino-functional silyl group, hydroxyl, acyloxy, ketoximino, amine, aminoxy, alkylamide, hydrogen, an aliphatic olefinic group, aryl, hydrosulfide, or a combination of two or more thereof.

14. The method of claim 13 wherein the reacting of the metal complexes with a silicon hydride-containing polyorganohydrosiloxane solution in solvent is under nitrogen atmosphere.

15. The method of claim 14, wherein the metal complex is selected from a metal salt chosen from PtCl$_2$, H$_2$PtCl$_6$, Pt$_2$(dba)$_3$, Pt$_2$(dvs)$_3$, Pt(OAc)$_2$ Pt(acac)$_2$, Na$_2$PtCl$_6$, K$_2$PtCl$_6$, platinum carbonate, platinum nitrate, 1,5-cycooctadienedimethylplatinum(II), platinum perchlorate, amine complexes of the platinum ammonium hexachloropalladate (IV), palladium(II) chloride, AuCl$_3$, Au$_2$O$_3$, NaAuO$_2$, AgCl, AgNO$_3$, CuSO$_4$, CuO, Cu(NO$_3$)$_2$, CuCl$_2$, Ru$_2$O$_3$, RuCl$_2$, FeCl$_2$.6H$_2$O, ZnCl$_2$, CoCl$_2$.6H$_2$O, NiCl$_2$.6H$_2$O, MnCl$_2$.4H$_2$O, TiCl$_4$, vanadium chloride, cadmium chloride, calcium chloride, zirconium tetrachloride, mercuric chloride complexes, or a combination of two or more thereof.

16. The method of claim 14, wherein encapsulating the metal nano-particles in the siloxane matrix comprises exposing the colloidal suspension to the presence of oxygen for a time period of from about 10 to about 30 minutes.

17. The method of claim 14 further comprising an optional step of removing at least about 50% of the solvent from the colloidal solution.

18. The method claim 13, wherein the ratio of polymer to metal complex ranges from about 0.001 to about 100.

19. The catalyst of claim 1, wherein the molecular weight of the polysiloxanes range from 100 to 50000, and the Si—H content of the polysiloxanes ranges from 0.001 to 99 mole percent.

20. The method claim 13, wherein the nanoparticles are chosen from at least one of aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, iridium, cerium, oxides and sulfides thereof.

21. The method of claim 13, wherein the step of (b) is carried out at a temperature between about 5 degree C. to about 150 degree C., and at a pressure ranging from 0.001 bar to 10 bar.

22. The method of claim 13, wherein said nanoparticles have a size in the range of from about 1 to about 100 nanometers.

23. The method of claim 13, wherein the reaction to form the colloidal suspension is carried out in the presence of a solvent.

24. The method claim 13, further comprising drying the supported nanoparticle catalysts.

25. The method of claim 13, wherein said support material comprises particles having a size in the range from 50 to 1000 micrometers.

26. The method of claim 13, wherein the ratio of metal loading to support material ranges from about 0.001 to 20 percent by weight.

27. The method of claim 13 wherein the support material comprises a functional group chosen from —Si—CH=CH$_2$, —Si—OH, —Si—(CH$_2$)$_n$C≡CH, —Si—(CH$_2$)$_n$—NH$_2$, —Si—(CH$_2$)$_n$—OH, —Si—(CH$_2$)$_n$—SH, or a combination of two or more thereof, and n is 1-26.

28. The method of claim 13, wherein the support material is functionalized with a hydrophobic group chosen from an alkyldisilazane, a vinyl-containing silazane, trimethyl disilazane, tetramethyl disilazane, pentamethyl disilazane, hexamethyl disilazane, octamethyl trisilazane, hexamethylcyclo trisilazane, tetraethyltetramethylcyclo tetrasilazane, tetraphenyldimethyl disilazane, dipropyltetramethyl disilazane, dibutyltetramethyl di silazazane, dihexyltetramethyl disilazane, dioctyltetramethyl disilazane, diphenyltetramethyl disilazane, octamethylcyclo tetrasilazane, or a combination of two or more thereof.

29. A process comprising:
(a) conducting a metal catalyzed reaction with a catalyst comprising a metal-containing polymer matrix of metal nanoparticles encapsulated in a siloxane polymer matrix covalently bonded to a support material,
wherein the siloxane polymer matrix comprises a cross-linked or partially crosslinked network of hydrosiloxanes with a vinyl silicone compound, the hydrosiloxanes are chosen from a silicon hydride-containing polyorganohydrosiloxane of the formula

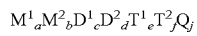

wherein: M$^1$=R$^1$R$^2$R$^3$SiO$_{1/2}$; M$^2$=R$^4$R$^5$R$^6$SiO$_{1/2}$; D$^1$=R$^7$R$^8$SiO$_{2/2}$; D$^2$=R$^9$R$^{10}$SiO$_{2/2}$; T$^1$=R$^{11}$SiO$_{3/2}$; T$^2$=R$^{12}$SiO$_{3/2}$; Q=SiO$_{4/2}$; R$^1$, R$^2$, R$^3$, R$^4$, R$^5$, R$^6$, R$^7$, R$^8$, R$^9$, R$^{10}$, R$^{11}$, and R$^{12}$ are aliphatic, aromatic or fluoro monovalent hydrocarbon having from 1 to 60 carbon atoms; at least one of R$^9$ or R$^{12}$ is hydrogen; and the subscript a, b, c, d, e, f, and j are zero or positive subject to the following limitations: 2≤a+b+c+d+e+f+j≤6000, and b+d+f>0, or (b) a monomer having a general formula R'$_m$H$_n$SiX$_{4-m-n}$, where each R' is independently selected from the group consisting of alkyls comprising one to 20 carbon atoms, cycloalkyls comprising four to 12 carbon atoms, and aryls; m=0 to 3, n=1 to 3, and m+n=1 to 4; each X is independently selected from a OR' group or a halide;
(b) recovering the catalyst; and
(c) conducting a subsequent metal catalyzed reaction with the recovered catalyst.

30. The process of claim 29, wherein the metal catalyzed reaction is chosen from hydrosilylation, hydroxylation, silaesterification, hydrogenation, oxidation, Heck and Suzuki coupling, dehydrocoupling.

31. The process according to claim 30 wherein the metal catalyzed reaction is a hydrosilylation reaction comprising a reaction of the silicon hydride and an unsaturated reactant.

32. The process of claim 31, wherein the silicon hydride is chosen from trimethylsilane, dimethylsilane, triethylsilane, dichlorosilane, trichlorosilane, methyldichlorosilane, dimethylchlorosilane, ethyldichlorosilane, cyclopentlydichlorosilane, methylphenylchlorosilane, (3,3,3-trifluoropropyl), heptamethyltrisiloxane hydride, triethoxysilane, trimethoxysilane, hydrogen terminated polydimethylsiloxane, monochlorosilane, or a combination of two or more thereof.

33. A process according to claim 31, wherein the unsaturated reactant is selected from the group consisting of a hydrocarbon compound or an unsaturated polyether.

34. The process of claim 31, wherein the unsaturated reactant is chosen from (CH$_2$=CH(CH$_2$)$_g$)$_h$R'$_i$Si(OR')$_{4-h-i}$ and (CH$_2$=CH(CH$_2$)$_g$R'$_i$SiCl$_{4-h-i}$, where R' is independently selected from the group consisting of alkyls comprising one to 20 carbon atoms, cycloalkyls comprising four to 12 carbon atoms, and aryls; g is 0 to 20, h is 1 to 3, I is 0-3, and h+i is 1 to 4.

35. The process of claim 33, where the hydrocarbon compounds is chosen from 1-hexene and 1-5 hexadiene, trans-2hexene, styrene, allylmethoxytriglycol, alpha-methylstyrene, eugenol, 1-octene, allyl glycidylether, trivinylcyclohexane, allylmethacrylate, allylamine, trichloroethylene, ally and vinyl ethers, dichlorostyrene, or a combination of two or more thereof.

36. The process of claim 33, wherein the unsaturated polyether is chosen from a blocked or random polyoxyalkylenes having at least one of the general formulas:

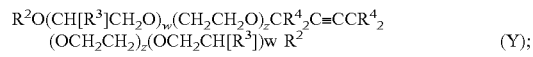

or

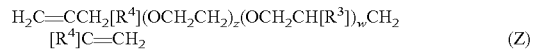

where R$^1$ denotes an unsaturated organic group containing from 3 to 10 carbon atoms; R$^2$ is hydrogen, or a polyether capping group of from 1 to 8 carbon atoms chosen from an alkyl group, an acyl group, or a trialkylsilyl group; R$^3$ and R$^4$ are monovalent hydrocarbon groups chosen from a C$_1$-C$_{20}$ alkyl group, an aryl group, an alkaryl group, or a cycloalkyl group; R$^4$ can also be hydrogen; z is 0 to 100 inclusive and w is 0 to 100 inclusive, with the proviso that z+w>0.

37. The process of claim 29, comprising repeating steps (b) and (c) two or more times.

38. The process of claim 29, wherein the recovered catalyst has a catalytic activity that is at least 85% of the catalytic activity of the catalyst in step (a).

39. The process of claim 29, wherein the recovered catalyst has a catalytic activity that is at least 95% of the catalytic activity of the catalyst in step (a).

40. The process of claim 29, wherein the recovered catalyst has a catalytic activity that is at least 99% of the catalytic activity of the catalyst in step (a).

41. The process according to claim 29, wherein the reaction is carried out in a batch, semi batch, or continuous mode at a temperature between about 0 degree C. to 500 degree C. and a pressure ranging from 0.01 bar to 100 bar.

42. The process of claim 29, wherein recovering the catalyst is accomplished by filtration.

43. The catalyst of claim 1, wherein the support material comprises particle having a size in the range of 50 to 1000 micrometers.

44. The catalyst of claim 1, wherein the support material is chosen from alumina, titania, zirconia, carbon nanotubes, synthetic zeolites, or natural zeolites.

45. The catalyst of claim 1, wherein the support material comprises a functional group chosen from allyl or vinyl.

46. The catalyst of claim 13, wherein the support material is chosen from alumina, titania, zirconia, carbon nanotubes, synthetic zeolites, or natural zeolites.

47. The catalyst of claim 13, wherein the support material comprises a functional group chosen from allyl or vinyl.

* * * * *